(12) United States Patent
Lombardi

(10) Patent No.: US 10,835,839 B1
(45) Date of Patent: *Nov. 17, 2020

(54) CANNABIS PRODUCTS MODIFIED BY REMOVING VOLATILE ORGANIC COMPOUNDS AND ADDING VOLATILE UNSATURATED HYDROCARBONS

(71) Applicant: HIGH SIERRA TECHNOLOGIES, INC., Reno, NV (US)

(72) Inventor: Vincent C. Lombardi, Reno, NV (US)

(73) Assignee: HIGH SIERRA TECHNOLOGIES, INC., Reno, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/912,031

(22) Filed: Jun. 25, 2020

Related U.S. Application Data

(63) Continuation of application No. 16/255,157, filed on Jan. 23, 2019, now Pat. No. 10,737,198.

(60) Provisional application No. 62/633,478, filed on Feb. 21, 2018, provisional application No. 62/620,726, filed on Jan. 23, 2018.

(51) Int. Cl.

| | | |
|---|---|---|
| *C07C 37/50* | (2006.01) | |
| *C07C 39/00* | (2006.01) | |
| *C07C 65/03* | (2006.01) | |
| *C07B 63/00* | (2006.01) | |
| *B01D 11/04* | (2006.01) | |
| *A61K 36/185* | (2006.01) | |
| *A61P 1/08* | (2006.01) | |
| *B01D 11/02* | (2006.01) | |
| *C07C 37/80* | (2006.01) | |
| *C11B 1/10* | (2006.01) | |
| *C07D 311/78* | (2006.01) | |
| *C07C 39/19* | (2006.01) | |

(52) U.S. Cl.
CPC ........ *B01D 11/0492* (2013.01); *A61K 36/185* (2013.01); *A61P 1/08* (2018.01); *B01D 11/0288* (2013.01); *C07B 63/00* (2013.01); *C07C 37/80* (2013.01); *C11B 1/10* (2013.01); *A61K 2236/37* (2013.01); *B01D 11/0296* (2013.01); *B01D 2257/70* (2013.01); *C07C 39/19* (2013.01); *C07C 65/03* (2013.01); *C07D 311/78* (2013.01)

(58) Field of Classification Search
CPC ......... C07C 37/50; C07C 39/19; C07C 65/03; C07B 63/00
See application file for complete search history.

(56) References Cited

U.S. PATENT DOCUMENTS

| | | |
|---|---|---|
| 6,403,126 B1 | 6/2002 | Webster et al. |
| 9,044,390 B1 | 6/2015 | Speier |
| 9,532,593 B2 | 1/2017 | Turner |
| 9,649,349 B1 | 5/2017 | Tucker et al. |
| 9,744,200 B1 | 8/2017 | Tucker et al. |
| 2005/0266108 A1 | 12/2005 | Flockhart et al. |
| 2009/0035396 A1 | 2/2009 | De Meijer |
| 2010/0197962 A1 | 8/2010 | Makovec et al. |
| 2014/0107192 A1 | 4/2014 | Maione et al. |
| 2014/0298511 A1 | 10/2014 | Lewis et al. |
| 2015/0105455 A1 | 4/2015 | Bjorncrantz |
| 2015/0297653 A1 | 10/2015 | Speier |
| 2016/0250270 A1 | 9/2016 | Wendschuh et al. |
| 2016/0300289 A1 | 10/2016 | Rose |
| 2017/0060907 A1 | 3/2017 | Raber et al. |
| 2017/0189463 A1 | 7/2017 | Franklin et al. |
| 2017/0202170 A1 | 7/2017 | Lewis et al. |
| 2017/0273349 A1 | 9/2017 | Moore |
| 2018/0296616 A1 | 10/2018 | Rivas |

FOREIGN PATENT DOCUMENTS

| | | |
|---|---|---|
| EP | 1385595 B1 | 5/2012 |
| WO | 2017/053731 A1 | 3/2017 |
| WO | 2018/044953 A1 | 3/2018 |

OTHER PUBLICATIONS

May 28, 2019 International Search Report issued in International Patent Application No. PCT/US19/14778.
May 28, 2019 Written Opinion of the International Searching Authority issued in International Patent Application No. PCT/US19/14778.
Dekker, Victoria. "Customize Your Cannabis Experience With Terpenes—Wherever You Are", Civilized, (2017), https://www.civilized.life/articles/cannabis-terpenes-experience/.
Sievers, A. F. et al., "Methods of Extracting Volatile Oils From Plant Material and the Production of Such Oils in the United States", Technical Bulletin, No. 16, (1928), pp. 1-28.
Babiker, Tayseer. "Charactization of Constituents of Catullus Colocynths Fixed Oil and Its Biological Activity", Sudan University of Science and Technology, (2017), pp. 1-49.

(Continued)

*Primary Examiner* — Sikarl A Witherspoon
(74) *Attorney, Agent, or Firm* — Oliff PLC

(57) ABSTRACT

Purified and modified *Cannabis* products and methods for producing the same. The purified *Cannabis* product comprises substantially no volatile organic compounds while retaining Total Potential cannabinoid content. The modified *Cannabis* product comprises a purified *Cannabis* product modified by at least one added volatile unsaturated hydrocarbon. The modified *Cannabis* product is formed by extracting a volatile organic compound from a *Cannabis* raw material to form a purified *Cannabis* product, and then adding the at least one volatile unsaturated hydrocarbon to the purified *Cannabis* product to form the modified *Cannabis* product and cause an enhanced user experience during combustion and inhalation of the modified *Cannabis* product.

57 Claims, 16 Drawing Sheets

(56) References Cited

OTHER PUBLICATIONS

McPartland, John et al., "Cannabis and Cannabis Extracts: Greater Than the Sum of Their Parts?", Journal of Cannabis Therapeutics, vol. 1, (2008), pp. 103-132.

Mar. 25, 2020 International Preliminary Report on Patentability issued in International Patent Application No. PCT/US2019/014778.

Sample: 1901TSF0055.0204

C-10

24.0% Total Potential THC 0.1% Total Potential CBD

Cannabinoids

| Cannabinoid | LOQ % | Mass % | Mass mg/g |
|---|---|---|---|
| THCa | 0.1 | 9.7 | 97 |
| Δ9-THC | 0.1 | 15.4 | 154 |
| Δ8-THC | 0.1 | <0.1 | <1 |
| CBD | 0.1 | ND | ND |
| CBDa | 0.1 | 0.1 | 1 |
| CBC | 0.1 | 0.1 | 1 |
| CBG | 0.1 | 0.2 | 2 |
| CBN | 0.1 | 0.1 | 1 |
| THCV | 0.1 | 0.1 | 1 |
| CBGa | 0.1 | 0.5 | 5 |
| Total | | 26.2 | 262 |

Sample: 1901TSF0055.0202

H-20

0.3%  
Total Potential THC 6.2%  
Total Potential CBD

Cannabinoids

| Cannabinoid | LOQ % | Mass % | Mass mg/g | |
|---|---|---|---|---|
| THCa | 0.1 | <0.1 | <1 | |
| Δ9-THC | 0.1 | 0.3 | 3 | ▨ |
| Δ8-THC | 0.1 | ND | ND | |
| CBD | 0.1 | 4.9 | 49 | ▬▬▬▬▬▬▬▬ |
| CBDa | 0.1 | 1.5 | 15 | ▬▬▬ |
| CBC | 0.1 | 0.5 | 5 | ▨ |
| CBG | 0.1 | 0.3 | 3 | ▨ |
| CBN | 0.1 | ND | ND | |
| THCV | 0.1 | ND | ND | |
| CBGa | 0.1 | 0.2 | 2 | ▨ |
| Total | | 7.6 | 76 | |

H-20

Terpenes

| Analyte | LOQ % | Mass % | Mass mg/g |
|---|---|---|---|
| α-Bisabolol | 0.05 | <0.05 | <0.5 |
| α-Humulene | 0.05 | <0.05 | <0.5 |
| β-Caryophyllene | 0.05 | <0.05 | <0.5 |
| β-Myrcene | 0.05 | ND | ND |
| β-Pinene | 0.05 | ND | ND |
| Caryophyllene Oxide | 0.05 | <0.05 | <0.5 |
| δ-Limonene | 0.05 | ND | ND |
| Linalool | 0.05 | ND | ND |
| Ocimene | 0.05 | ND | ND |
| Terpinolene | 0.05 | ND | ND |
| trans-Nerolidol | 0.05 | <0.05 | <0.5 |
| α-Pinene |  | ND | ND |

Primary Aromas

Total Terpenes

CANNABIS PRODUCTS MODIFIED BY REMOVING VOLATILE ORGANIC COMPOUNDS AND ADDING VOLATILE UNSATURATED HYDROCARBONS

CROSS-REFERENCE TO RELATED APPLICATIONS

This application is a Continuation of application Ser. No. 16/255,157, filed Jan. 23, 2019, which claims priority to Provisional Application No. 62/620,726, filed Jan. 23, 2018, and Provisional Application No. 62/633,478, filed Feb. 21, 2018. The contents of the prior applications are hereby incorporated by reference in their entireties.

TECHNICAL FIELD

This application relates to methods for purifying and modifying a *Cannabis* product by first removing volatile organic compounds and then adding volatile unsaturated hydrocarbons to produce a modified *Cannabis* product for recreational and medicinal use.

BACKGROUND

*Cannabis* is a genus of flowering plants in the family of Cannabaceae and includes at least three known species: *Cannabis sativa*, *Cannabis indica* and *Cannabis ruderalis*. Marijuana and Hemp are forms of *Cannabis*. Marijuana includes all varieties of the *Cannabis* genus that contain substantial amounts of THC and is conventionally used for recreational or medicinal purposes. Hemp includes all varieties of the *Cannabis* genus that contain negligible amounts of THC and generally refers to the industrial, non-drug variant of *Cannabis* that is cultivated for its flower leaf material, fiber, hurd, and seeds. Hemp flower is used in the production of CBD oils, ointments and extracts used in various dietary supplements as well as the production of Hemp cigarettes that contain CBD compounds. The Hemp seed is mainly used in dietary products and can also be pressed and made into oil that can be used as salad dressing, paint, ink, and as a core ingredient in many body care products. The Hemp stalk and its fiber have more than 25,000 industrial uses, including mainly clothing, construction materials, paper, apparel, bags, rope, netting, canvas, and carpet. Hemp hurds can be used in cement, insulation, paper, animal bedding, biodegradable garden mulch, and plastics.

Through selective breeding or genetic modification, several varieties or strains of *Cannabis* have been produced, all of which are considered *Cannabis*. *Cannabis* is used as a drug or medicine for medicinal and recreation uses. It is consumed through smoking (combustion and inhalation) *Cannabis* plant material, plant extracts or purified or modified compounds, or through ingestion of the plant material, plant extracts or purified or modified compounds. The most commonly recognized biologically active components of *Cannabis* include Δ9-tetrahydrocannabinol (THC) and cannabidiol (CBD). At least 483 known compounds are found in *Cannabis* including at least 113 other cannabinoids which may have a yet unidentified medicinal benefit.

*Cannabis* can be used by smoking the dried plant material, by smoking of extracts of the plant material, or by orally consuming with food, or by consuming as an extract. To date, thirty-three States, the District of Columbia, Guam and Puerto Rico have passed laws allowing *Cannabis* to be used for a variety of medical conditions. Ten states and the District of Columbia have adopted laws legalizing *Cannabis* for recreational use. The non-medical use of *Cannabis* has been decriminalized in thirteen States and the U.S. Virgin Islands. In addition, Canada has legalized both medicinal and recreational *Cannabis* in all provinces as of Oct. 17, 2018, and Canada legalized the growing and use of Hemp for any and all commercial purposes as of May of 1998.

As of Dec. 20, 2018, with the enactment of the 2018 Farm Bill, Hemp, which is defined in the Bill as the plant *Cannabis sativa* L. and any part of that plant, including the seeds thereof and all derivatives, extracts, cannabinoids, isomers, acids, salts, and salts of isomers, whether growing or not, with a THC concentration of not more than 0.3 percent on a dry weight basis, has become legal in all fifty states and is no longer considered a controlled substance subject to regulation by the United States Drug Enforcement Agency.

*Cannabis* has a distinct strong and pungent odor, primarily as a result of several volatile small molecules known as terpenes and collectively described as essential oils. Terpenes are ubiquitous throughout the plant world and are produced by a myriad of plant species. Terpenes are commonly found in fruits, vegetables, herbs, spices, and other botanicals. They are also common ingredients in the human diet and have generally been recognized as safe to consume by the United States Food and Drug Administration. The general class of molecules that encompass terpenes can be further broken down into mono-terpenes, diterpenes and sesquiterpenes, sesterterpenes, triterpenes, sesquarterpenes, tetraterpenes, polyterpenes, and norisoprenoids, contingent on the number of repeating units of a five-carbon molecule referred to as isoprene which is the structural hallmark of all terpenoid compounds. The term terpenoid is used to describe a derivative of a terpene. Terpenes are among the volatile unsaturated hydrocarbons found in the essential oils of many types of plants and flowers. Essential oils are used widely as fragrances in perfumery and in medicine and alternative medicines such as aromatherapy. Synthetic variations and derivatives of natural terpenes (terpenoids) greatly expand the possible numbers of potential terpenoids which could be used to modify the flavor and aroma of *Cannabis*.

Although terpenes may possess some medical benefits, the flavor and smell that results from the presence of these terpenes may be found undesirable by many users of *Cannabis*. Moreover, the strong and pungent odor can linger for hours in the environment, as well as in the clothing of the individuals present during smoking. Because the odor is distinct and easily recognizable as that of *Cannabis*, it is difficult to smoke *Cannabis* with discretion, which presents a limitation on their use. Since *Cannabis*-based products may be used for medicinal purposes, the removal of this strong and pungent odor is especially desirable.

Some processes for the extraction of *Cannabis* compounds are known. While conventional compound extraction processes are generally known, these processes remain inefficient and cost-ineffective due to the number of variables. None of the conventional processes contemplate selectively extracting a volatile organic compound, such as a terpene (natural or synthetic), from a *Cannabis* raw plant material to form a purified *Cannabis* product, where the purified *Cannabis* product retains the desired naturally occurring Total Potential cannabinoid content (i.e., an amount of naturally occurring cannabinoid plus any decarboxylated cannabinoid acids) in the *Cannabis* raw material after the extraction.

Additionally, the resulting products tend to exhibit reduced efficacy and/or substandard odor and flavor due to the "wholesale" removal of desired ingredients along with the compound targeted for removal. In this regard, it is not conventionally known to selectively extract terpenes while retaining substantially all of the Total Potential cannabinoid content, or to further modify a previously-modified *Cannabis* product, where the previously-modified or purified *Cannabis* product is substantially free of a target compound or compounds that detracts from a desired user experience. Further, current methods to isolate the potential cannabinoids, commonly called "extractions" result in the significant loss of the terpenes and the plant structure.

Accordingly, there is a need for a comprehensive and cohesive approach to process *Cannabis* to provide a low, or no, odor and/or reduced or modified flavor form of *Cannabis*, with minimal loss of plant structure. In this regard, if the volatile organic compounds such as essential oils, including terpenes (natural or synthetic) were to be removed without affecting the Total Potential cannabinoid content, the *Cannabis* could be used without leaving a strong and obvious odor on the user or subjecting the user to what may be deemed to be an unpleasant taste. These and other advantages are exhibited by the following disclosed embodiments.

SUMMARY

Disclosed embodiments provide purified and modified *Cannabis* products without the above-described drawbacks in order to create a more desirable experience for the user in terms of the odor and flavor of the inhaled product, while at the same time preserving the naturally occurring Total Potential cannabinoid content thereof and leaving both the purified and the modified *Cannabis* raw plant material undamaged and still in a condition that it can be smoked in the same manner as before it was modified.

To this end, the disclosed embodiments are directed to novel *Cannabis* products that do not produce the characteristic odor and flavor typically associated with the smoking (combustion and subsequent inhalation) of unmodified *Cannabis* plant material and methods of removing or significantly reducing the volatile organic molecules from *Cannabis* raw plant material ("primary modification"). Further, new and novel *Cannabis* products are then provided that have new and unique odors and flavors that exist as modified *Cannabis* products by methods of further modifying the primarily modified *Cannabis* products by adding volatile unsaturated hydrocarbons, either naturally occurring or synthetically produced, including, but not limited to, essential oils, flavorings or terpenes (natural or synthetic) ("secondary modification").

In a first embodiment, there is provided a purified *Cannabis* product. The purified *Cannabis* product comprises cannabinoids, and substantially no volatile organic compounds. The purified *Cannabis* product is formed by selectively extracting the volatile organic compounds from a *Cannabis* raw plant material to form the purified *Cannabis* product. Substantially all of a naturally occurring potential cannabinoid content in the raw plant material is retained in the purified *Cannabis* product after the extraction, and substantially all of a naturally occurring physical structure of the *Cannabis* product is retained in the purified *Cannabis* product after the extraction so that the purified *Cannabis* product can be combusted and inhaled in a manner similar to a naturally occurring *Cannabis* product under similar conditions.

In another embodiment, there is provided a modified *Cannabis* product. The modified *Cannabis* product comprises cannabinoids, and at least one volatile unsaturated hydrocarbon. The modified *Cannabis* product is formed by extracting volatile organic compounds from a *Cannabis* raw plant material to form a purified *Cannabis* product, and then adding the at least one volatile unsaturated hydrocarbon to the purified *Cannabis* product to form the modified *Cannabis* product and cause an enhanced user experience during combustion and inhalation of the modified *Cannabis* product.

In another embodiment, there is provided a method for producing a purified *Cannabis* product. The method comprises selectively extracting volatile organic compounds from a *Cannabis* raw plant material to form a purified *Cannabis* product. The purified *Cannabis* product retains substantially all of a naturally occurring potential cannabinoid content in the raw plant material after the extraction.

In another embodiment, there is provided a method for producing a modified *Cannabis* product. The method comprises adding at least one volatile organic compound to a purified *Cannabis* product to form the modified *Cannabis* product. The purified *Cannabis* product is substantially free of terpene content.

In another embodiment, there is provided a method for producing a modified *Cannabis* product. The method comprises extracting a first volatile organic compound from a *Cannabis* raw plant material to form a purified *Cannabis* product, and then adding at least one second volatile organic compound to the purified *Cannabis* product to form the modified *Cannabis* product. The second volatile organic compound is different than the first volatile organic compound.

In another embodiment, there is provided a purified *Cannabis* product comprising cannabinoids and substantially no terpenes. The product is formed by selectively extracting volatile organic compounds from a *Cannabis* raw plant material to form the purified *Cannabis* product. Substantially all of a naturally occurring potential cannabinoid content in the raw plant material is retained in the purified *Cannabis* product after the extraction.

In another embodiment, there is provided a modified *Cannabis* product comprising cannabinoids and at least one volatile unsaturated hydrocarbon. The product is formed by extracting a volatile organic compound from a *Cannabis* raw plant material to form a purified *Cannabis* product, and then adding the at least one volatile unsaturated hydrocarbon to the purified *Cannabis* product to form the modified *Cannabis* product. The at least one volatile unsaturated hydrocarbon is different than the volatile organic compound, and substantially all of a naturally occurring potential cannabinoid content in the raw plant material is retained in the purified *Cannabis* product after the extraction.

BRIEF DESCRIPTION OF THE DRAWINGS

The disclosed embodiments will now be described with reference to the following figures.

DETAILED DESCRIPTION

Figure 1:
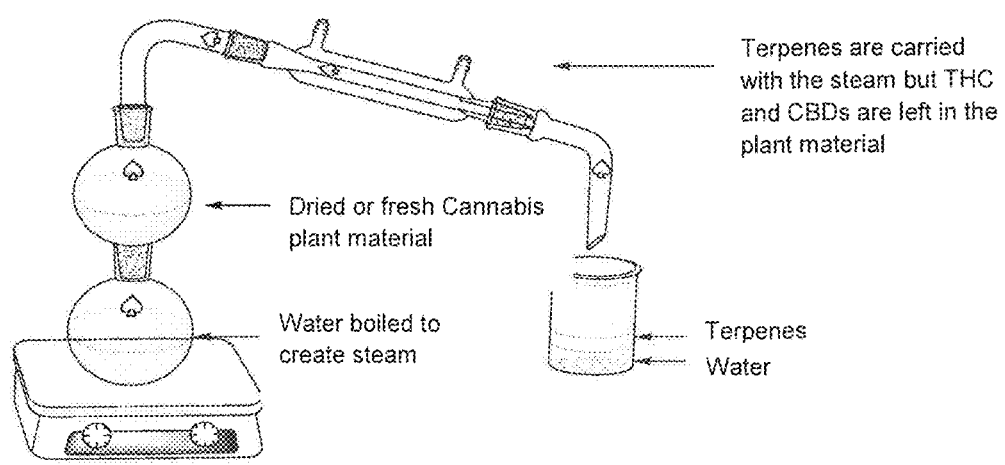
FIG. 1 illustrates a steam extraction system that can be used for primary modification of *Cannabis* raw plant material according to an embodiment.

As used herein, Cannabis includes any plant or plant material derived from a Cannabis plant (i.e., Cannabis sativa, Cannabis indica and Cannabis ruderalis), naturally or through selective breeding or genetic engineering. The Cannabis may be used for therapeutic, medicinal, research, recreational purposes or any yet unforeseen purpose. Ways for consuming Cannabis according to embodiments may include, but are not limited to, inhalation by smoking dried Cannabis plant material, inhalation by smoking Cannabis plant extracts or by ingesting Cannabis plant material or plant extracts such as, for example, in the form of edible Cannabis products that incorporate raw plant material, where potentially undesirable odor and/or taste has been removed and a possibly more desirable odor/taste has been added to the raw plant material. For purposes of this disclosure, the disclosed embodiments will be described with respect to the production of a modified form of dried Cannabis plant material for consumption by inhalation after combustion. It will be understood that the disclosed products and methods may apply to all types, forms and uses of Cannabis.

As used herein, as stated, Marijuana includes all varieties of the Cannabis genus that contain substantial amounts of THC. As used herein, Hemp includes all varieties of the Cannabis genus that contain negligible amounts of THC. Hemp specifically includes the plant Cannabis sativa L. and any part of that plant, including the seeds thereof and all derivatives, extracts, cannabinoids, isomers, acids, salts, and salts of isomers, whether growing or not, with a THC concentration defined according to relevant regulations. For example, the 2018 Farm Bill and many states define Hemp as having a THC concentration of not more than 0.3 percent on a dry weight basis. Many states have adopted similar definitions. Notably, West Virginia defines Hemp as Cannabis with a THC concentration of less than 1 percent. Many state definitions for industrial Hemp specify that THC concentration is on a dry weight basis and can be measured from any part of the plant. Some states also require the plant to be possessed by a licensed grower for it to be considered under the definition of industrial Hemp.

In the embodiments, there are provided purified Cannabis products comprising naturally occurring cannabinoids and substantially no volatile organic compounds and modified Cannabis products comprising naturally occurring and/or decarboxylated cannabinoids and at least one volatile unsaturated hydrocarbon. In other embodiments, there are provided methods for selectively extracting volatile organic compounds from a Cannabis raw material to form a purified Cannabis product (primary modification) and adding at least one volatile organic compound to a purified Cannabis product to form a modified Cannabis product (secondary modification).

Volatile Organic Compounds

It is commonly known that the characteristic smell and flavor of Cannabis when smoked is primarily the result of a class of small volatile organic molecules known as terpenes. Terpenes are a primary constituent of the essential oil extract of Cannabis. Therefore, the disclosed embodiments provide a Cannabis product that is produced by removing or reducing the naturally occurring compliment of volatile organic molecules from Cannabis, which primarily consist of terpenes, and are collectively known as the essential oils. At least 200 terpenes are found in the Cannabis plant but 14 are commonly found in significant quantities, which vary in quantity depending on the strain of the Cannabis plant. The molecular structure of these common terpenes, i.e., isoprene, α-pinene, β-pinene, Δ3-carene, d-limonene, camphene, myrcene, β-phellandrene, sabinene, α-terpinene, ocimene, α-thujene, terpinolene and γ-terpinene, are shown below.

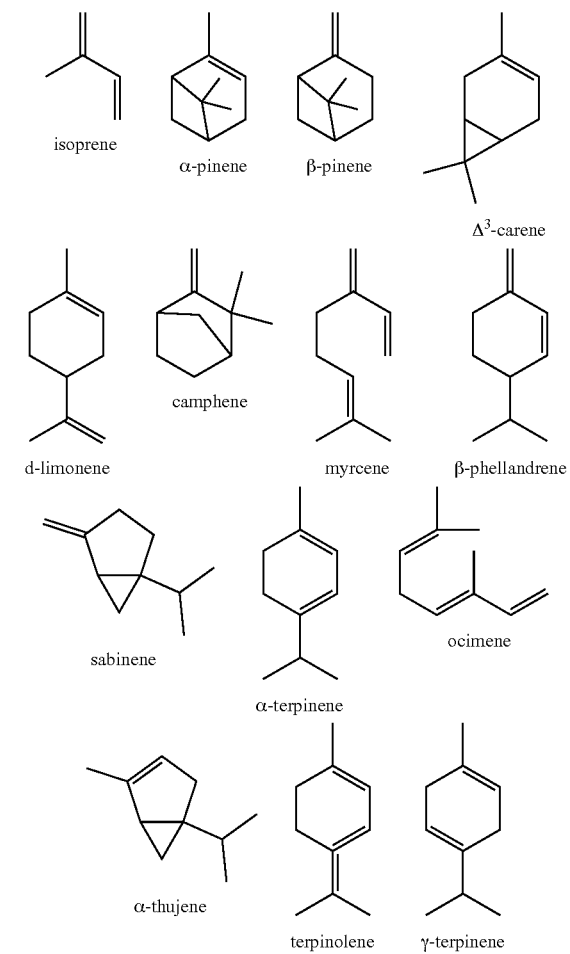

Terpenes serve as the precursors for the synthesis of chemicals used in the production of food, cosmetics, and are regularly used in the pharmaceutical and biotechnology industries. Chemical synthesis of terpenes can be challenging in light of their complex structure, and since most plants produce them is small amounts, extracting terpenes from natural plant sources is often difficult, time-consuming and cost-prohibitive. To date, the genomes of 17 plant species have been shown to contain the genes that encode terpenoid synthase enzymes imparting terpenes with their basic structure, as well as the enzyme cytochrome P450s, which is required to modify this basic structure. It is believed that all known terpenes are synthesized by the enzyme terpene synthase.

Terpenes are biosynthetically produced from units of isoprene, which has the basic molecular formula $C_5H_8$. The molecular formula of terpenes is a multiple of that molecular formula, $(C_5H_8)^n$ where n is the number of linked isoprene residues. This is commonly referred to as the isoprene rule or sometimes the C5 rule. The isoprene units can be linked together "head to tail" to form straight chains and can also be arranged to form rings. Indeed, the isoprene unit is one of nature's most common building blocks. As chains of isoprene units are synthesized, the resulting terpenes are classified consecutively according to their size as hemiterpenes, monoterpenes, sesquiterpenes, diterpenes, sesterterpenes, triterpenes, tetraterpenes and polyterpenes.

Terpenes may be categorized by the number of isoprene units that make up the molecule. The number of terpene units that make up the molecule is designated by the prefix of the name. For example, hemiterpenes consist of a single isoprene unit. Isoprene is considered the only hemiterpene, but oxygen-containing derivatives such as prenol and isovaleric acid are hemiterpenoids.

Monoterpenes consist of two isoprene units and have the molecular formula $C_{10}H_{16}$. Examples of monoterpenes and monoterpenoids include geraniol, terpineol (present in lilacs), myrcene (present in hops), limonene (present in citrus fruits), linalool (present in lavender) and pinene (present in conifers).

Sesquiterpenes consist of three isoprene units and have the molecular formula $C_{15}H_{24}$. Examples of sesquiterpenes include humulene (also known as α-humulene or α-caryophyllene), and farnesene, which refers to a set of six closely related chemical compounds which all are sesquiterpenes (the sesqui-prefix indicates one and a half).

Diterpenes are composed of four isoprene units, which have the molecular formula $C_{20}H_{32}$ and are derive from geranylgeranyl pyrophosphate; an intermediate in the biosynthesis of some terpenes and terpenoids. Examples of diterpenes and diterpenoids are cafestol, kahweol, cembrene and taxadiene (precursor of taxol). Diterpenes also form the basis for biologically important compounds such as retinol, retinal, and phytol.

Sesterterpenes, which have 25 carbons and five isoprene units, are rare relative to the other terpenes (the sester-prefix means half to three, i.e., two and a half). An example of a sesterterpenoid is geranylfarnesol.

Triterpenes comprise six isoprene units and have the molecular formula $C_{30}H_{48}$. An example of a triterpenes is squalene, the main constituent of shark liver oil. Squalene can also be biosynthetically processed to generate lanosterol or cycloartenol, the structural precursors to all the steroids.

Sesquarterpenes are composed of seven isoprene units and have the molecular formula $C_{35}H_{56}$. Sesquarterpenes are typically microbial in their origin. Examples of sesquarterpenoids are ferrugicadiol and tetraprenylcurcumene.

Tetraterpenes contain eight isoprene units and have the molecular formula $C_{40}H_{64}$. Biologically important tetraterpenoids include the acyclic lycopene, the monocyclic gamma-carotene, and the bicyclic alpha- and beta-carotenes.

Polyterpenes consist of long chains of many isoprene units. Natural rubber consists of polyisoprene in which the double bonds are cis. Some plants produce a polyisoprene with trans double bonds, known as gutta-percha.

Norisoprenoids, such as the C13-norisoprenoids 3-oxo-α-ionol present and 7,8-dihydroionone derivatives, such as megastigmane-3,9-diol and 3-oxo-7,8-dihydro-α-ionol found in Muscat of Alexandria and Shiraz leaves, respectively (grapes in the species *Vitis vinifera*) are responsible for some of the spice in Chardonnay, can be produced by fungal peroxidases or glycosidases.

Isoprene itself does not directly feed into the biosynthetic pathway but rather the activated forms, isopentenyl pyrophosphate (IPP or also isopentenyl diphosphate) and dimethylallyl pyrophosphate (DMAPP or also dimethylallyl diphosphate), are the components in the biosynthetic pathway. IPP is formed from acetyl-CoA via the intermediacy of mevalonic acid in the HMG-CoA reductase pathway.

In addition to these terpenes, cannabinoids are also found in *Cannabis*. These cannabinoids do not appreciably contribute to the complement of organic molecules found in the essential oils. The molecular structure of nine cannabinoids found in *Cannabis* produced under elevated temperature are shown below.

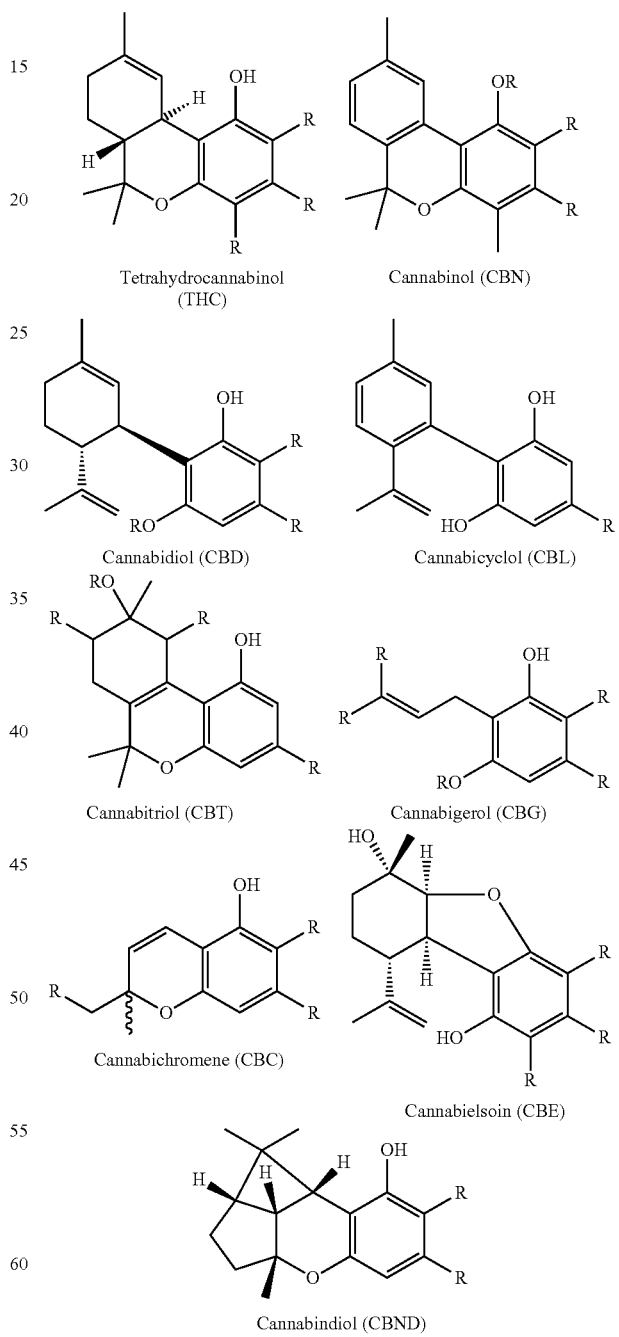

Purified *Cannabis* Product

A purified *Cannabis* product according to the disclosed embodiments includes naturally occurring cannabinoids, and substantially no volatile organic compounds. The purified Cannabis product is formed by selectively extracting the volatile organic compounds from a Cannabis raw plant material to form the purified Cannabis product. Substantially all of a naturally occurring potential cannabinoid content in the raw material is retained in the purified Cannabis product after the extraction, and substantially all of a naturally occurring physical structure of the Cannabis product is retained in the purified Cannabis product after the extraction so that the purified Cannabis product can be combusted and inhaled in a manner similar to a naturally occurring Cannabis product under similar conditions.

A method (i.e., primary modification) for forming the purified Cannabis product is as follows. In the embodiments, Cannabis raw plant material is subjected to any process that removes or significantly reduces the amount of volatile organic compounds, such as essential oils or terpenes, without removing a significant amount of the naturally occurring Total Potential of cannabinoids (e.g., THC and CBD), or negatively impacting the naturally occurring physical structure of the original Cannabis plant material. The amount of naturally occurring Total Potential cannabinoid content retained from the Cannabis depends on the desired purified product (i.e., the degree of activity based on desired user experience). In embodiments, substantially all of the Total Potential cannabinoid content may be retained. Alternatively, 5%, 10%, 20%, 30%, 40%, 50%, 60%, 70%, 80%, 90%, 99% or 99.9%, by mass %, of the Total Potential cannabinoid content may be retained. Depending on the desired purified product, the amount of Total Potential cannabinoid content retained may be in a range of 25% to 100%, 50% to 99.9%, 75% to 99%, 90% to 99%, 50% to 99%, 70% to 99.9%, 80% to 99%, or 90% to 99.9%, by mass %. Preferably, as much of the naturally occurring Total Potential cannabinoid content is retained as possible.

The amount of volatile organic compound removed from the Cannabis depends on the desired purified product (i.e., the degree of purity based on desired user or patient experience). In embodiments, substantially all of the compound may be removed. Alternatively, 5%, 10%, 20%, 30%, 40%, 50%, 60%, 70%, 80%, 90%, 99% or 99.9%, by mass %, of the compound may be removed. Depending on the desired purified product, the amount of compound removed may be in a range of 25% to 100%, 50% to 99%, 70% to 99.9% or 90% to 99.9%, by mass %.

It will be understood that the terms "remove," "removal," "reduce," "reduction," and the like, when used in the context of the disclosed processes are meant to imply the removal or reduction of a significant amount of a substance or chemical but that it may not be practical for most such processes to remove or reduce 100% of a substance or a chemical. It will also be understood that the terms "retain," "retained," and the like, when used in the context of the disclosed processes are meant to imply the retention of a significant amount of a substance or chemical but that it may not practical for most such processes to retain 100% of a substance or a chemical. Accordingly, it will be understood that "substantial" removal/retention or "substantially" removing/retaining for the purposes of this disclosure may include a tolerance known or generally accepted in the cannabis and chemical processing industries. For example, "substantial" removal/retention or "substantially" removing/retaining may include a tolerance in a range of 0 to 5%, 0.001 to 5%, 0.01 to 5%, 0.1 to 5%, 0.001 to 1%, 0.01 to 1%, 0.1 to 1%, 0.001 to 0.1%, or 0.001 to 0.01%.

In the purified Cannabis product, the ratio of an amount of cannabinoids (e.g., THC and CBD), to the remaining amount of volatile organic compound, such as a terpene, may be in the range of 100:0, 10:90, 25:75, 50:50, 60:40, 75:25, 90:10, 95:5, or 99:1, by mass %. Similarly, the ratio of an amount of the total amount of non-volatile organic compound ingredients to the remaining amount of volatile organic compound, may be in the range of 100:0, 10:90, 25:75, 50:50, 60:40, 75:25, 90:10, 95:5, or 99:1, by mass %.

Methods of producing the primarily modified Cannabis product by removing the essential oils of naturally occurring Cannabis raw plant material may include any suitable method known in the art. For example, methods of producing the primarily modified Cannabis product by removing the essential oils of naturally occurring Cannabis raw plant material may include, but are not limited to, passing steam over the material, volatizing the essential oils through reduced atmospheric pressure and/or increased temperature, extraction with an organic and/or non-organic liquid, expression, absolute oil extraction, resin tapping, cold pressing, selective breeding or genetic engineering or modification (e.g., genetically engineering without or with a defective terpene synthase gene), or any combination of the above-described methods or processes.

In the embodiments, removal of terpenes from Cannabis may be affected by use of a steam extraction apparatus 10 that may be used to isolate the essential oils from plants, as shown in FIG. 1. In this system, water is boiled below the Cannabis and the steam is allowed to pass through the Cannabis raw plant material. The starting material can be either dried or undried unmodified Cannabis raw plant material. Because the boiling point of the terpenes is lower than the boiling point of water, the terpenes are volatilized by the steam and are carried with the steam into a condenser that cools the steam and terpenes back to a temperature below their boiling point. The condensed water and terpenes then flow into a collection flask. Because the boiling point of cannabinoids are much greater than that of water or terpenes, the cannabinoids are retained in the Cannabis raw plant material. The Table below illustrates the boiling points associated with common terpenes and cannabinoids found in Cannabis.

| List of Common Terpenes and Cannabinoids Found in Cannabis |||||||
|---|---|---|---|---|---|---|
| Terpenes |||| Cannabinoids* |||
| Name | M.W. (g/mol) | B.P. (° C.) | M.P. (° C.) | Name | M.W. (g/mol) | B.P.# (° C.) | M.P. (° C.) |
| Isoprene | 68.11 | 34.1 | −145.9 | Δ9-tetrahydrocannabinol | 314.46 | 390.4 ± 42.0 | 200 |
| α-pinene | 136.23 | 157.9 | −55 | Cannabinol | 310.43 | 476.5 | 76-77 |
| β-pinene | 136.23 | 166 | −61 | Cannabidiol (-trans) | 314.46 | 463.9 ± 45.0 | 62-63 |
| Carene | 136.23 | 171.4 | <25 | Cannabicyclol | 314.46 | 382.1 | N/A |
| D-Limonene | 136.23 | 175.4 | −74 | Cannabitriol | 346.46 | 418 | 176 |
| Camphene | 136.23 | 157.5 | 35 | Cannabigerol | 316.48 | 470.4 | 49-52 |

-continued

List of Common Terpenes and Cannabinoids Found in *Cannabis*

| | Terpenes | | | | Cannabinoids* | | |
|---|---|---|---|---|---|---|---|
| Name | M.W. (g/mol) | B.P. (° C.) | M.P. (° C.) | Name | M.W. (g/mol) | B.P.# (° C.) | M.P. (° C.) |
| Myrcene | 136.23 | 167 | −10 | Cannabichromene | 314.46 | 428.7 ± 45.0 | N/A |
| β-phellandrene | 136.23 | 175 | −40 | Cannabielsoin | 330.46 | N/A | N/A |
| Sabinene | 136.23 | 164 | N/A | Cannabinodiol | 310.43 | 497.3 ± 40.0 | N/A |
| α-terpinene | 136.23 | 174.1 | −40 | Tetrahydrocannabivarin | 286.41 | 360.6 | N/A |
| Ocimene | 136.23 | 170.2 | 50 | Cannabidivarin | 286.41 | 439.4 ± 45.0 | N/A |
| α-thujene | 136.23 | 152 | N/A | Cannabichromevarin | 286.41 | 401.4 ± 45.0 | N/A |
| Terpinolene | 136.23 | 182 | <25 | | | | |
| γ-terpinene | 136.23 | 183 | 60-61 | | | | |

*Represents the decarboxylated form of the naturally occurring acid
At 760 mmHg
Values from www.chemsrc.com or http://www.chemspider.com when available In conventional processes of extracting essential oils using a steam extraction apparatus, the essential oils are separated from the water based on density and the plant material is discarded. However, according to the disclosed embodiments, the desired product is the extracted plant material. After the essential oils have been extracted, the *Cannabis* is then dried to remove any residual water that results from the process. The result of this process is a *Cannabis* product from which the essential oils, including the terpenes, have been removed and substantially all of the naturally occurring Total Potential cannabinoid content has been retained.

Figure 2:
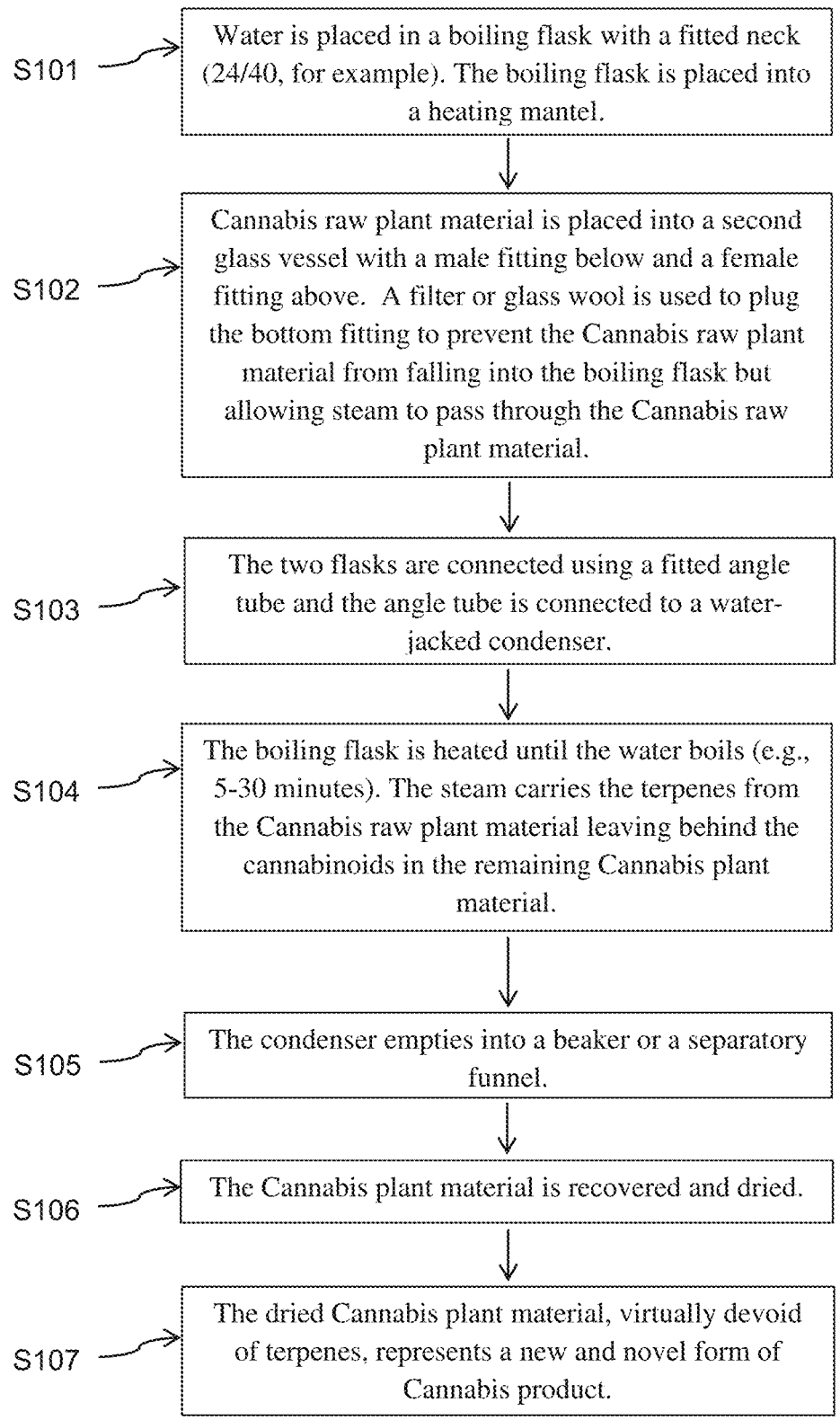
FIG. 2 illustrates a steam extraction process that can be used for primary modification of *Cannabis* raw plant material according to an embodiment.

As seen in FIG. 2, the process begins with water being placed in a boiling flask with a fitted neck (e.g., 24/40) and the boiling flask being placed into a heating mantel (S101). *Cannabis* raw plant material is the placed into a second glass vessel with a male fitting below and a female fitting above, and a filter or glass wool is used to plug the bottom fitting to prevent the *Cannabis* raw plant material from falling into the boiling flask but allowing steam to pass through the raw plant material (S102). The two flasks are then connected using a fitted angle tube and the angle tube that is connected to a water-jacked condenser (S103). Subsequently, the boiling flask is heated until the water boils (e.g., 5-30 minutes), and the steam carries the terpenes from the *Cannabis* leaving behind the cannabinoids in the *Cannabis* plant material (S104). The steam may be passed through the *Cannabis* raw plant material for any suitable duration of time. For example, the duration may be in the range of 1 to 120 minutes, 1 to 30 minutes, 5 to 30 minutes, or 10 to 20 minutes. The condenser empties into a beaker or a separatory funnel (S105). The *Cannabis* plant material is then recovered and dried (S106 and S107). The dried *Cannabis* plant material, then virtually devoid of terpenes, represents the primarily modified *Cannabis* product.

Figure 3:
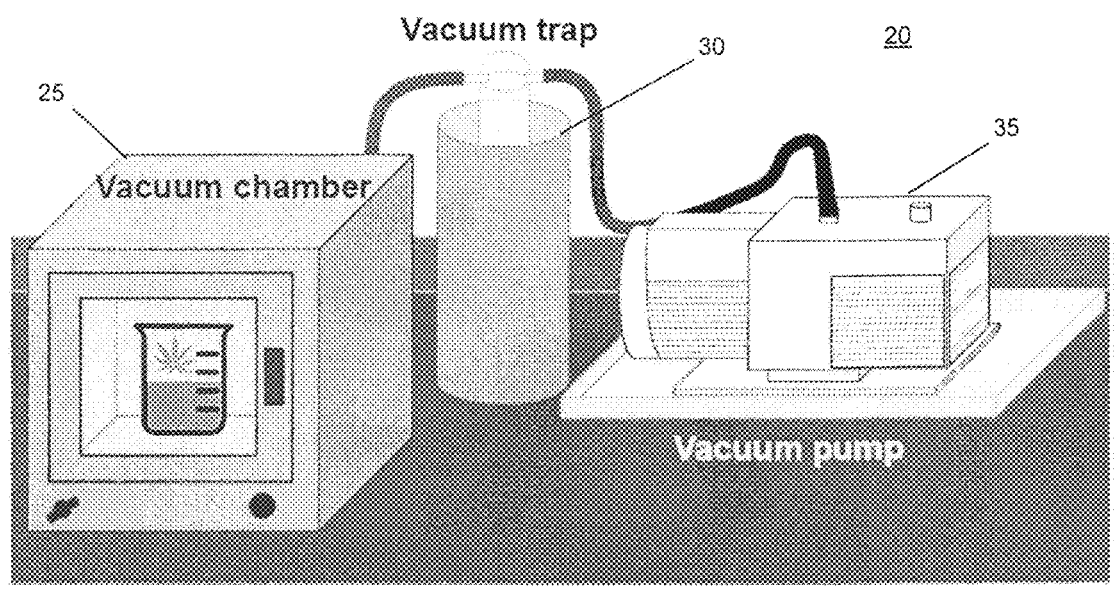
FIG. 3 illustrates a vacuum desiccation system that can be used for primary modification of *Cannabis* raw plant material according to an embodiment.

In the embodiments, the essential oils may be removed using a vacuum desiccation system 20. As shown in FIG. 3, the harvested plant material is placed in a vacuum chamber 25 that is sealed, and vacuum is applied via the vacuum trap 30 and vacuum pump 35. The boiling point of any given liquid is the temperature at which the vapor pressure of the liquid equals the pressure surrounding the liquid. By reducing the pressure sufficiently, a liquid can be made to boil at room temperature. For example, in the embodiments, the boiling point of isoprene, a terpene naturally occurring in *Cannabis*, is lowered by 0.0382° C. per millimeter of mercury decreased from atmospheric pressure (760 mm), as described in Bekkedahl, N., Wood, L. A. & Wojciechowski, M. Some Physical Properties of Isoprene, *Journal of Research of the National Bureau of Standards*, 17, 883-894 (1936). Accordingly, isoprene will boil or volatilize at room temperature (25° C.) when the atmospheric pressure is reduced by 235 mm of mercury. Because the boiling point of cannabinoids is significantly higher than that of terpenes, they are retained in the *Cannabis* raw plant material that has been processed under reduced atmospheric pressure.

Modified *Cannabis* Product

A modified *Cannabis* product according to the disclosed embodiments is formed by extracting volatile organic compounds from *Cannabis* raw plant material to form a purified *Cannabis* product, and then adding at least one volatile unsaturated hydrocarbon to the purified *Cannabis* product to form the modified *Cannabis* product, which results in an enhanced user experience during combustion and inhalation of the modified *Cannabis* product.

Using a primarily modified *Cannabis* product from which the volatile organic compounds have been extracted, removed or significantly reduced as the starting material for the further modification of the odor and flavor of the primarily modified *Cannabis* product by way of introducing, or adding, novel combinations of the various volatile unsaturated hydrocarbons found in the essential oils of other plants or derivatives thereof, or synthetically produced volatile chemicals, alters the odor and flavor of the primarily modified *Cannabis* product to make it more desirable to *Cannabis* users that prefer a more acceptable odor and flavor.

The modification of the odor and flavor of *Cannabis* experienced when the *Cannabis* product is combusted and inhaled can be achieved by adding any volatile unsaturated hydrocarbon, naturally occurring or synthetic, in any suitable combination to the primarily modified *Cannabis* product from which the naturally occurring volatile organic compounds have been substantially removed or reduced to form a secondarily modified *Cannabis* product. In the embodiments, the volatile unsaturated hydrocarbons may include, but are not limited to, naturally occurring or synthetic terpene compounds, terpenoid compounds, essential oil compounds, ester compounds, aldehyde compounds, alcohol compounds, and mixtures and/or derivatives thereof.

The terpene compounds added may include, but are not limited to, one or more of any specific class of naturally occurring or synthetic hemiterpenes, monoterpenes, sesquiterpenes, diterpenes, sesterterpenes, triterpenes, sesquarterpenes, tetraterpenes, or polyterpenes, and mixtures or derivatives thereof, or specific terpenes including, but not limited to, isoprene, α-pinene. β-pinene, Δ3-carene, d-limonene, camphene, myrcene, β-phellandrene, sabinene, α-terpinene, ocimene, α-thujene, terpinolene, γ-terpinene, and mixtures or derivatives thereof.

The terpenoid compounds added may include, but are not limited to, one or more of any specific class of naturally occurring or synthetic terpenoids such as hemiterpenoids, monoterpenoids, sesquiterpenoids, diterpenoids, sesterterpenoids, triterpenoids, tetraterpenoids, polyterpenoid, and mixtures or derivatives thereof.

The essential oil compounds added may include, but are not limited to, one or more of any specific class of naturally occurring or synthetic *cannabis, angelica*, basil, bergamot, Roman chamomile, German chamomile, cinnamon bark, citrus rind, clary sage, clove, coriander, dill, *eucalyptus globulus*, frankincense, *galbanum*, geranium, ginger, grapefruit, hyssop, Idaho blue spruce, juniper, jasmine, *Laurus nobilis*, lavender, lemon, lemongrass, lime, lemonbalm, marjoram, myrrh, myrtle, nutmeg, orange, oregano, patchouli, pepper, peppermint, petitgrain, pine, rosemary, rose, savory, sage, sandalwood, spearmint, spruce, tarragon, tangerine, thyme, valerian, vetiver, ylang ylang, and mixtures or derivatives thereof.

Moreover, the aldehyde compounds, ester compounds, and alcohol compounds are not specifically limited. It will be understood that any suitable aldehyde compound, ester compound, alcohol compound, other compound that provides odor and flavor of the primarily modified *Cannabis* product to make it more desirable to *Cannabis* is within the scope of this disclosure.

Figure 4:
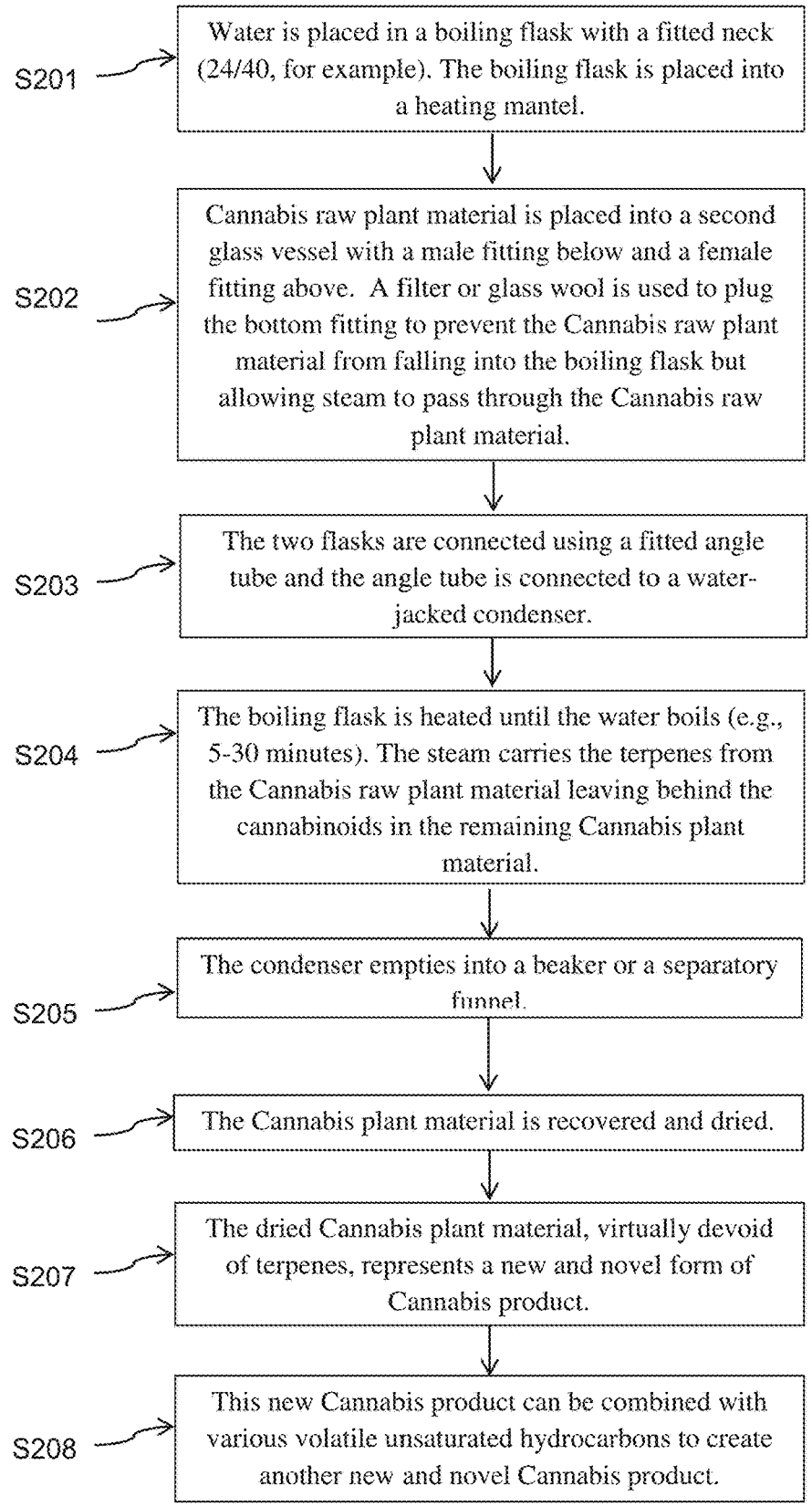
FIG. 4 illustrates a secondary modification process of primarily modified *Cannabis* raw plant material according to an embodiment.

A method (i.e., secondary modification) for forming the modified *Cannabis* product is as follows. The primary modified *Cannabis* product, i.e., a *Cannabis* product from which the essential oils have been extracted, removed or significantly reduced for the purpose of modifying the odor and flavor experienced when the plant or plant material is combusted and inhaled, may then be subjected to secondary modification. With reference to FIG. 4, this process may include providing a primarily modified *Cannabis* product according the first embodiment (i.e., steps S201, S202, S203, S204, S205, S206 and S207). For example, the primary modified *Cannabis* product may be a product formed according to the primary modification process discussed herein. Subsequently, various volatile unsaturated hydrocarbons are added to the primarily modified *Cannabis* product (S208).

In the embodiments, the secondary modification process may include any combination or mixture of the above-described compounds, i.e., additive or modification "profiles." The profiles may include specific compounds including concentrations that are known or determined to have specific scents, effects, etc. The profiles may be specified (i.e., according to a predetermined "recipe") or unspecified according random selection. The effectiveness or user preference may recorded for future use in, e.g., ranking flavors or medicinal or therapeutic benefits.

EXAMPLES

The following examples are illustrative of the disclosed embodiments. All tests were performed using HPLC-UV. It is known that decarboxylation of THC and CBD acids occur during any smoking or cooking process, i.e., changing of the THC and CBD acids into THC and CBD. Therefore, the actual amount of THC and CBD differs from the amount of "Total Potential" THC and CBD. In the examples, the liquid chromatography analysis occurs at room temperature and does not decarboxylate any THC or CBD, thereby yielding separate values for THCa, THC, CBDa and CBD, which are then combined to derive the Total Potential THC and Total Potential CBD result using the following formulae:

Total Potential THC=THCa*0.877+Δ9-THC

Total Potential CBD=CBDa*0.877+CBD

Moreover, the following abbreviations/notes apply throughout the examples:

ND=Non Detect

LOQ=Limit of Quantitation

Cannabinoids for flower and trim reported as received.

Examples 1-3 represent three different Marijuana samples selected from the same strain. Examples 4-6 represent three different Hemp samples selected from the same strain. Example 1 (sample C-0) and Example 4 (H-0) represent the control groups and were analyzed for cannabinoid and terpene content without application of the disclosed steam extraction process. Example 2 (sample C-10) and Example 5 (H-10) were subjected to 10 minutes of the disclosed steam extraction process and then analyzed for cannabinoid and terpene content. Example 3 (sample C-20) and Example 6 (H-20) were subjected to 20 minutes of the disclosed steam extraction process and then analyzed for cannabinoid and terpene content. The results are illustrated below.

Example 1

| | C-0 | | |
| --- | --- | --- | --- |
| Analyte | LOQ (%) | Mass (%) | Mass (mg/g) |
| Cannabinoids | | | |
| THCa | 0.1 | 17.8 | 178 |
| Δ9-THC | 0.1 | 1 | 10 |
| Δ8-THC | 0.1 | 0.2 | 2 |
| CBD | 0.1 | ND | ND |
| CBDa | 0.1 | 0.1 | 1 |
| CBC | 0.1 | <0.1 | <1 |
| CBG | 0.1 | 0.1 | 1 |
| CBN | 0.1 | ND | ND |
| THCV | 0.1 | ND | ND |
| CBGa | 0.1 | 0.6 | 6 |
| Total | | 19.7 | 197 |
| Total Potential THC | 16.8% | | |
| Total Potential CBD | 0.1% | | |
| Terpenes | | | |
| β-Caryophyllene | 0.05 | 0.56 | 5.6 |
| δ-Limonene | 0.05 | 0.16 | 1.6 |
| α-Humulene | 0.05 | 0.14 | 1.4 |
| Linalool | 0.05 | 0.05 | 0.5 |
| α-Pinene | | 0.02 | 0.2 |
| α-Bisabolol | 0.05 | <0.05 | <0.5 |
| β-Myrcene | 0.05 | <0.05 | <0.5 |
| β-Pinene | 0.05 | <0.05 | <0.5 |
| Caryophyllene Oxide | 0.05 | <0.05 | <0.5 |
| Ocimene | 0.05 | ND | ND |
| Terpinolene | 0.05 | ND | ND |
| trans-Nerolidol | 0.05 | <0.05 | <0.5 |

Example 2

C-10

| Analyte | LOQ (%) | Mass (%) | Mass (mg/g) |
|---|---|---|---|
| Cannabinoids | | | |
| THCa | 0.1 | 9.7 | 97 |
| Δ9-THC | 0.1 | 15.4 | 154 |
| Δ8-THC | 0.1 | <0.1 | <1 |
| CBD | 0.1 | ND | ND |
| CBDa | 0.1 | 0.1 | 1 |
| CBC | 0.1 | 0.1 | 1 |
| CBG | 0.1 | 0.2 | 2 |
| CBN | 0.1 | 0.1 | 1 |
| THCV | 0.1 | 0.1 | 1 |
| CBGa | 0.1 | 0.5 | 5 |
| Total | | 26.2 | 262 |
| Total Potential THC | 24.0% | | |
| Total Potential CBD | 0.1% | | |
| Terpenes | | | |
| β-Caryophyllene | 0.05 | 0.22 | 2.2 |
| α-Humulene | 0.05 | 0.07 | 0.7 |
| α-Bisabolol | 0.05 | 0.07 | 0.7 |
| trans-Nerolidol | 0.05 | 0.05 | 0.5 |
| β-Myrcene | 0.05 | ND | ND |
| β-Pinene | 0.05 | ND | ND |
| Caryophyllene Oxide | 0.05 | <0.05 | <0.5 |
| δ-Limonene | 0.05 | <0.05 | <0.5 |
| Linalool | 0.05 | <0.05 | <0.5 |
| Ocimene | 0.05 | ND | ND |
| Terpinolene | 0.05 | ND | ND |
| α-Pinene | | ND | ND |

Example 3

C-20

| Analyte | LOQ (%) | Mass (%) | Mass (mg/g) |
|---|---|---|---|
| Cannabinoids | | | |
| THCa | 0.1 | 4.7 | 47 |
| Δ9-THC | 0.1 | 16.9 | 169 |
| Δ8-THC | 0.1 | ND | ND |
| CBD | 0.1 | ND | ND |
| CBDa | 0.1 | <0.1 | <1 |
| CBC | 0.1 | 0.1 | 1 |
| CBG | 0.1 | 0.3 | 3 |
| CBN | 0.1 | 0.1 | 1 |
| THCV | 0.1 | 0.1 | 1 |
| CBGa | 0.1 | 0.4 | 4 |
| Total | | 22.6 | 226 |
| Total Potential THC | 21.1% | | |
| Total Potential CBD | <LOQ | | |
| Terpenes | | | |
| α-Bisabolol | 0.05 | 0.08 | 0.8 |
| β-Caryophyllene | 0.05 | 0.05 | 0.5 |
| α-Humulene | 0.05 | <0.05 | <0.5 |
| β-Myrcene | 0.05 | ND | ND |
| β-Pinene | 0.05 | ND | ND |
| Caryophyllene Oxide | 0.05 | <0.05 | <0.5 |
| δ-Limonene | 0.05 | ND | ND |
| Linalool | 0.05 | ND | ND |
| Ocimene | 0.05 | ND | ND |
| Terpinolene | 0.05 | ND | ND |
| trans-Nerolidol | 0.05 | <0.05 | <0.5 |
| α-Pinene | | ND | ND |

Example 4

H-0

| Analyte | LOQ (%) | Mass (%) | Mass (mg/g) |
|---|---|---|---|
| Cannabinoids | | | |
| THCa | 0.1 | 0.4 | 4 |
| Δ9-THC | 0.1 | ND | ND |
| Δ8-THC | 0.1 | ND | ND |
| CBD | 0.1 | 0.1 | 1 |
| CBDa | 0.1 | 10.5 | 105 |
| CBC | 0.1 | <0.1 | <1 |
| CBG | 0.1 | <0.1 | <1 |
| CBN | 0.1 | ND | ND |
| THCV | 0.1 | ND | ND |
| CBGa | 0.1 | 0.9 | 9 |
| Total | | 11.9 | 119 |
| Total Potential THC | 0.4% | | |
| Total Potential CBD | 9.3% | | |
| Terpenes | | | |
| β-Myrcene | 0.05 | 0.61 | 6.1 |
| β-Caryophyllene | 0.05 | 0.48 | 4.8 |
| α-Humulene | 0.05 | 0.15 | 1.5 |
| α-Pinene | | 0.13 | 1.3 |
| Ocimene | 0.05 | 0.06 | 0.6 |
| α-Bisabolol | 0.05 | <0.05 | <0.5 |
| β-Pinene | 0.05 | <0.05 | <0.5 |
| Caryophyllene Oxide | 0.05 | <0.05 | <0.5 |
| δ-Limonene | 0.05 | <0.05 | <0.5 |
| Linalool | 0.05 | <0.05 | <0.5 |
| Terpinolene | 0.05 | ND | ND |
| trans-Nerolidol | 0.05 | <0.05 | <0 |

Example 5

H-10

| Analyte | LOQ (%) | Mass (%) | Mass (mg/g) |
|---|---|---|---|
| Cannabinoids | | | |
| THCa | 0.1 | 0.1 | 1 |
| Δ9-THC | 0.1 | 0.4 | 4 |
| Δ8-THC | 0.1 | ND | ND |
| CBD | 0.1 | 5.2 | 52 |
| CBDa | 0.1 | 4.6 | 46 |
| CBC | 0.1 | 0.7 | 7 |
| CBG | 0.1 | 0.2 | 2 |
| CBN | 0.1 | ND | ND |
| THCV | 0.1 | ND | ND |
| CBGa | 0.1 | 0.3 | 3 |
| Total | 11.5 | 115 | |
| CBGa | 0.1 | 0.3 | 3 |
| Total | | 11.5 | 11.5 |
| Total Potential THC | 0.4% | | |
| Total Potential CBD | 9.3% | | |
| Terpenes | | | |
| β-Caryophyllene | 0.05 | 0.05 | 0.5 |
| α-Bisabolol | 0.05 | <0.05 | <0.5 |
| α-Humulene | 0.05 | <0.05 | <0.5 |
| β-Myrcene | 0.05 | ND | ND |
| β-Pinene | 0.05 | ND | ND |
| Caryophyllene Oxide | 0.05 | <0.05 | <0.5 |
| δ-Limonene | 0.05 | ND | ND |
| Linalool | 0.05 | ND | ND |

-continued

H-10

| Analyte | LOQ (%) | Mass (%) | Mass (mg/g) |
|---|---|---|---|
| Ocimene | 0.05 | ND | ND |
| Terpinolene | 0.05 | ND | ND |
| trans-Nerolidol | 0.05 | <0.05 | <0.5 |
| α-Pinene |  | ND | ND |

Example 6

H-20

| Analyte | LOQ (%) | Mass (%) | Mass (mg/g) |
|---|---|---|---|
| Cannabinoids | | | |
| THCa | 0.1 | <0.1 | <1 |
| Δ9-THC | 0.1 | 0.3 | 3 |
| Δ8-THC | 0.1 | ND | ND |
| CBD | 0.1 | 4.9 | 49 |
| CBDa | 0.1 | 1.5 | 15 |
| CBC | 0.1 | 0.5 | 5 |
| CBG | 0.1 | 0.3 | 3 |
| CBN | 0.1 | ND | ND |
| THCV | 0.1 | ND | ND |
| CBGa | 0.1 | 0.2 | 2 |
| Total |  | 7.6 | 76 |
| Total Potential THC | 0.3% | | |
| Total Potential CBD | 6.2% | | |
| Terpenes | | | |
| α-Bisabolol | 0.05 | <0.05 | <0.5 |
| α-Humulene | 0.05 | <0.05 | <0.5 |
| β-Caryophyllene | 0.05 | <0.05 | <0.5 |
| β-Myrcene | 0.05 | ND | ND |
| β-Pinene | 0.05 | ND | ND |
| Caryophyllene Oxide | 0.05 | <0.05 | <0.5 |
| δ-Limonene | 0.05 | ND | ND |
| Linalool | 0.05 | ND | ND |
| Ocimene | 0.05 | ND | ND |
| Terpinolene | 0.05 | ND | ND |
| trans-Nerolidol | 0.05 | <0.05 | <0.5 |
| α-Pinene |  | ND | ND |

Figure 5A:
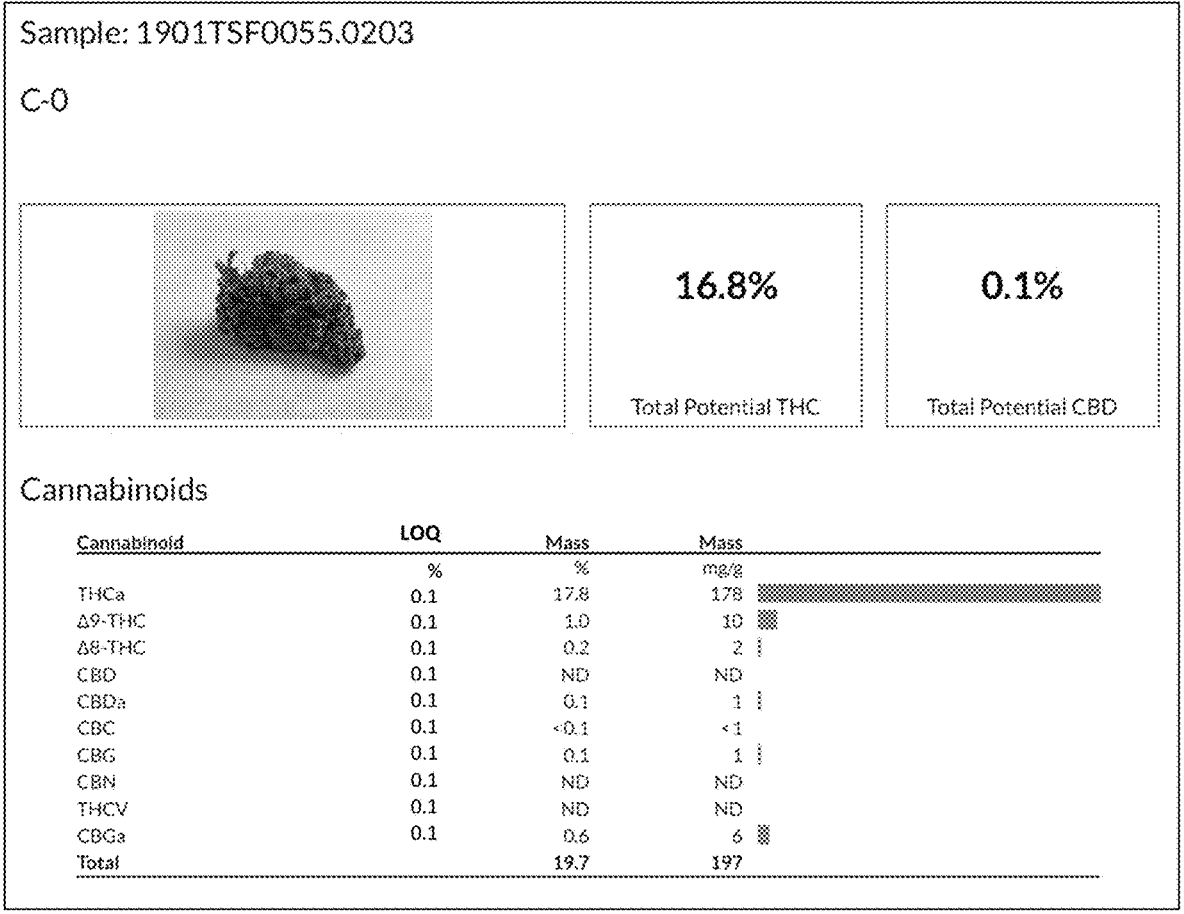
FIGS. 5A-5F illustrate analytical results of Marijuana samples according to embodiments.
Figure 5B:
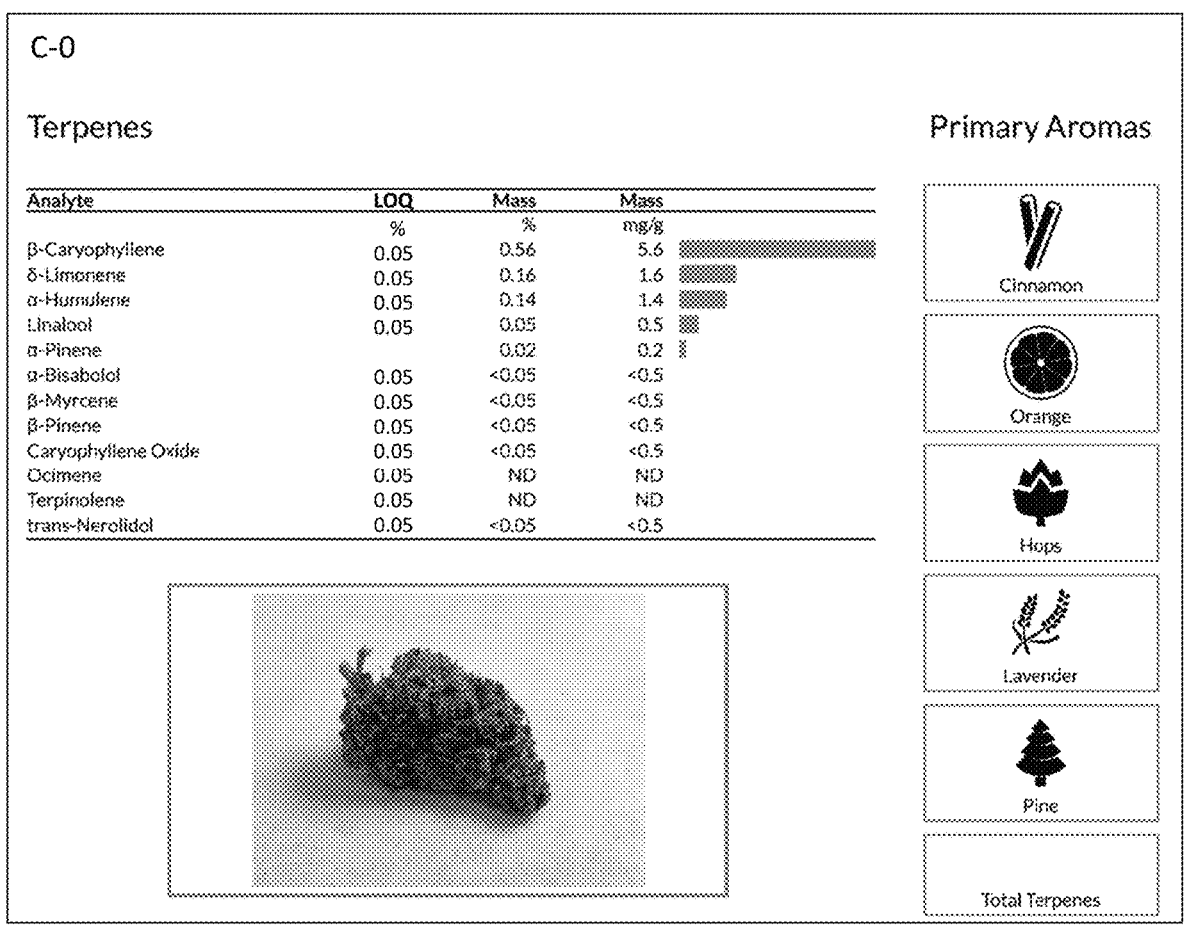
Figure 5C:
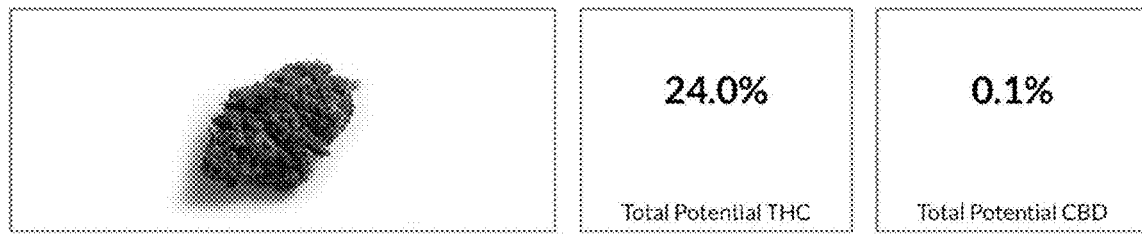
Figure 5D:
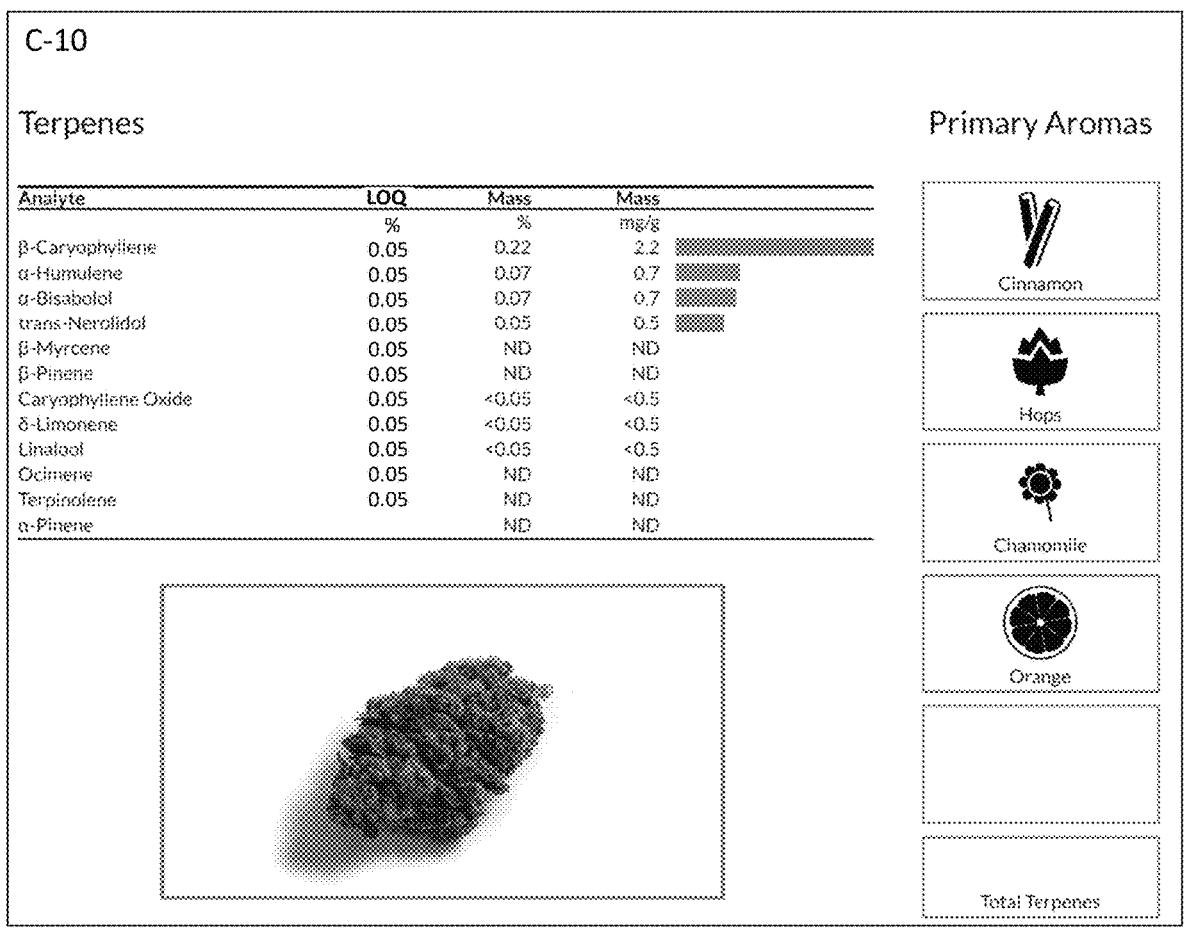
Figure 5E:
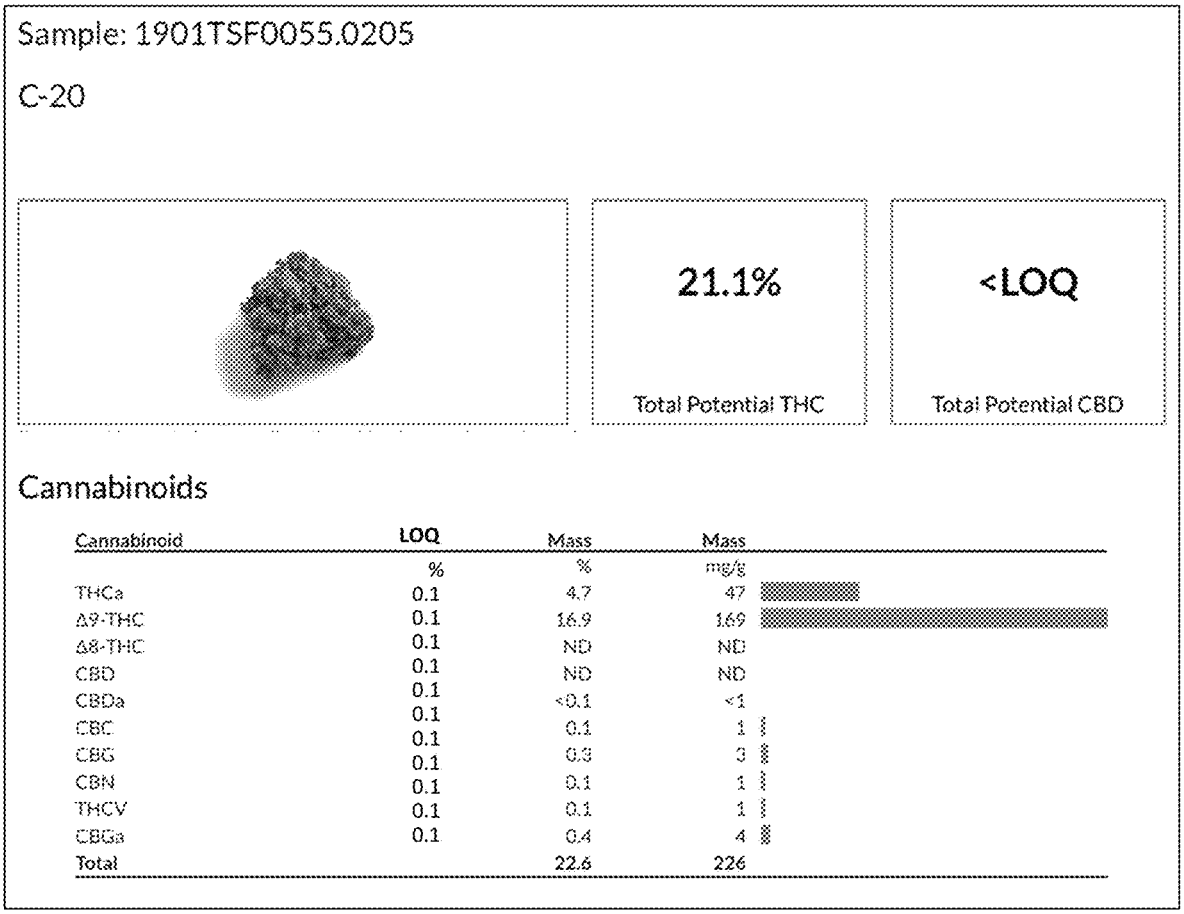
Figure 5F:
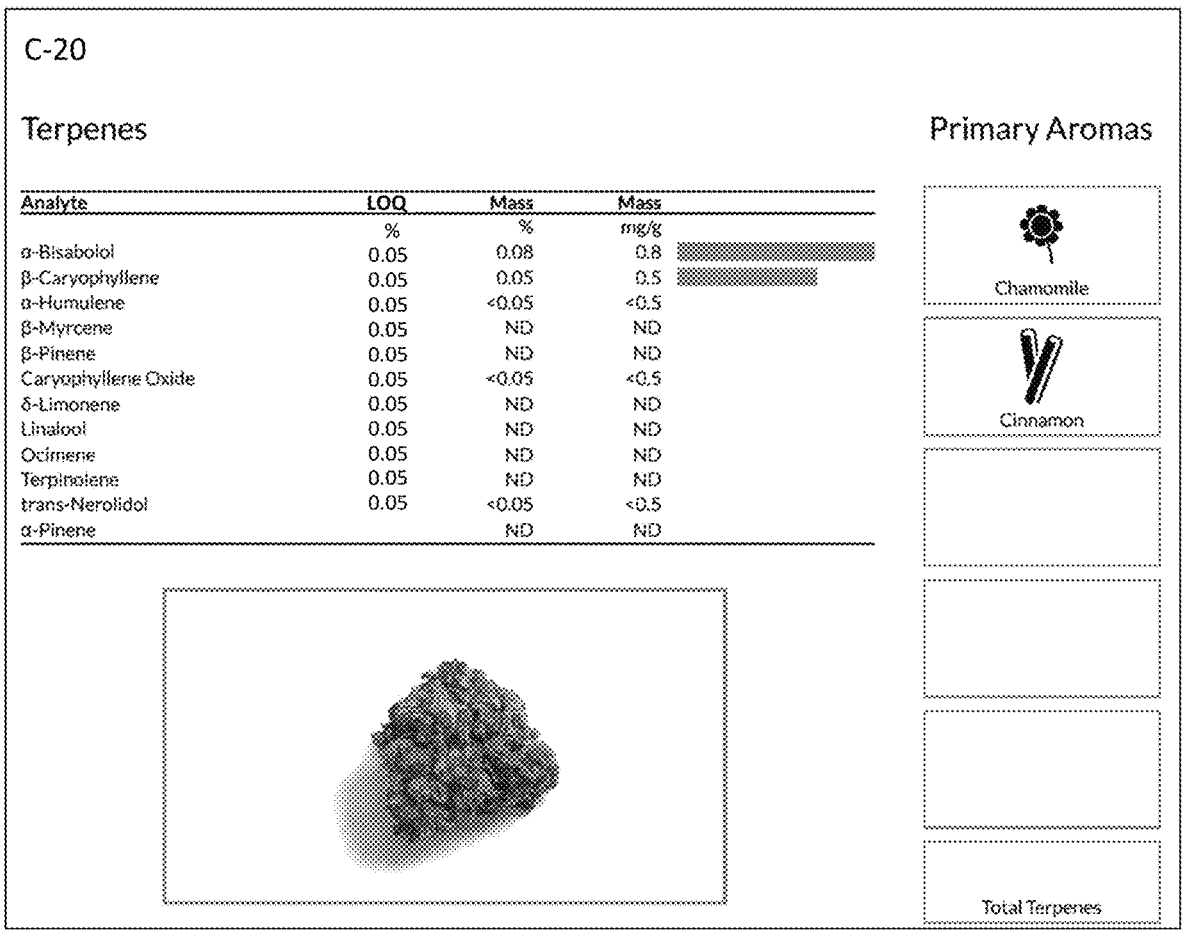
Figure 6A:
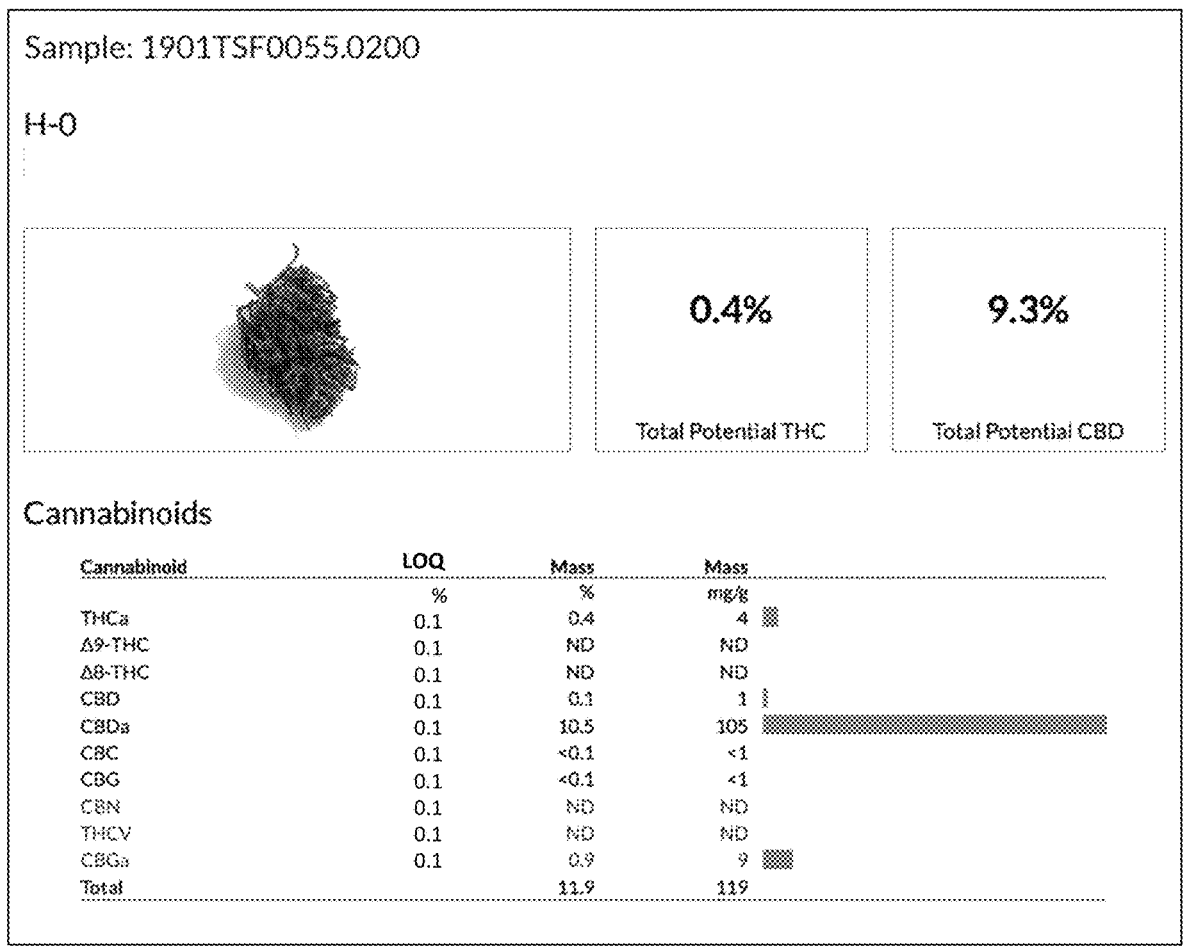
FIGS. 6A-6F illustrate analytical results of Hemp samples according to embodiments.
Figure 6B:
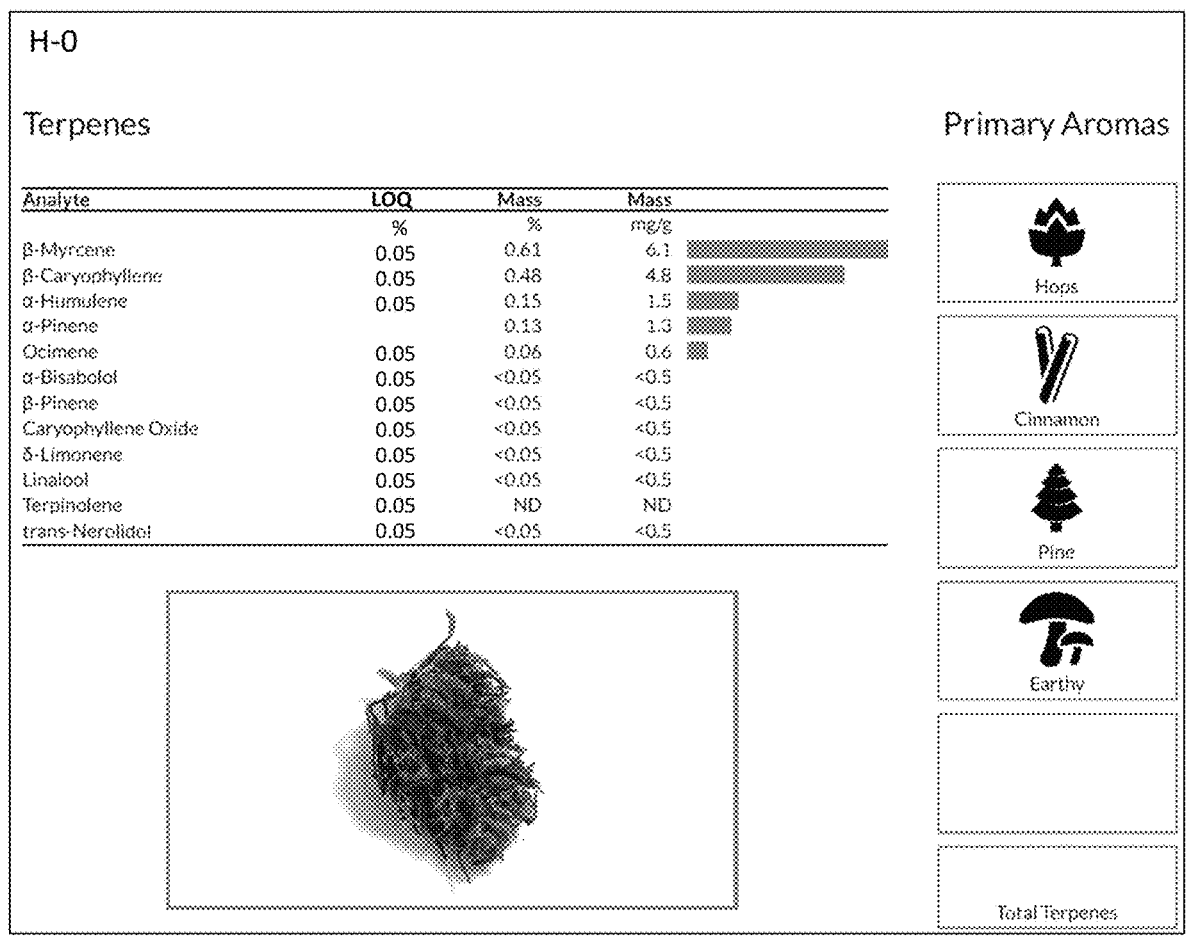
Figure 6C:
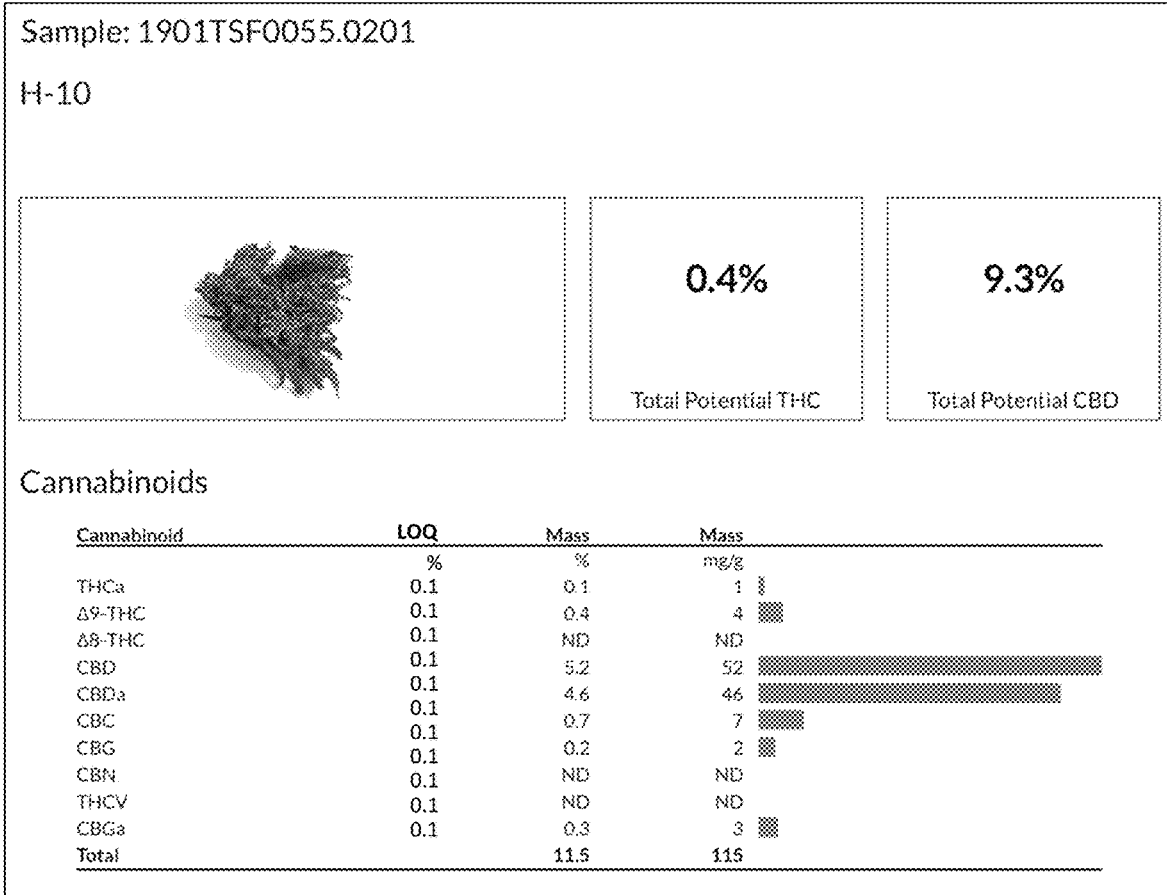
Figure 6D:
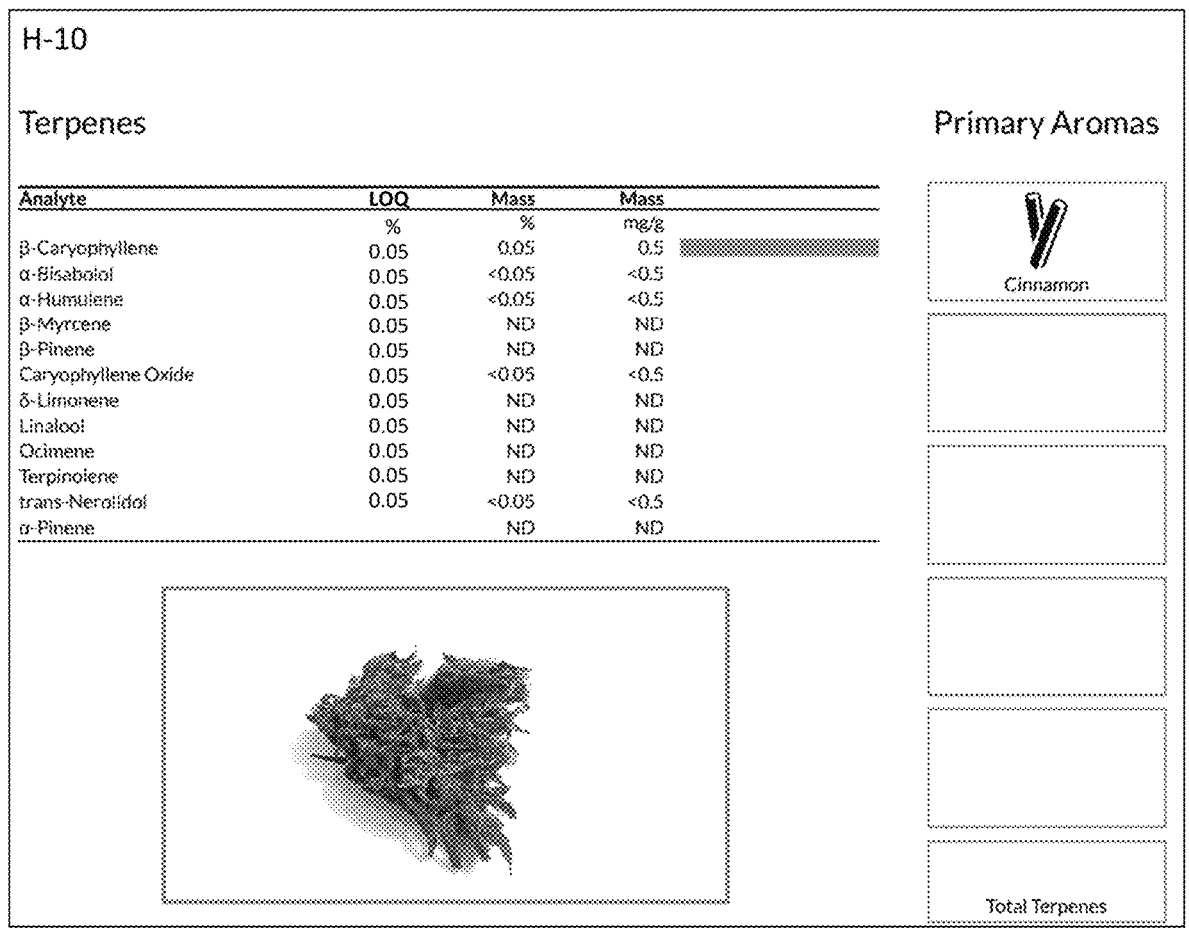
Figure 6E:
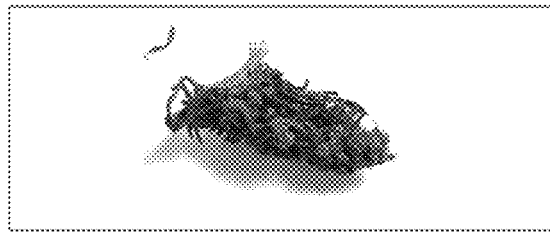
Figure 6F:
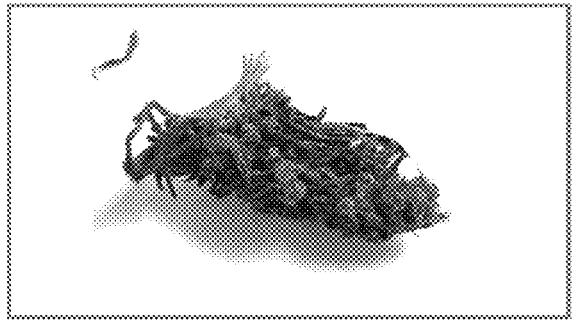

The results of the cannabinoid content analysis of the Marijuana samples in Examples 1, 2 and 3 are illustrated in graphical format in FIGS. 5A, 5C and 5E, respectively. The results of the terpene content analysis of the Marijuana samples in Examples 1, 2 and 3 are illustrated in graphical format in FIGS. 5B, 5D and 5F, respectively. The results of the cannabinoid content analysis of the Hemp samples in Examples 4, 5 and 6 are illustrated in graphical format in FIGS. 6A, 6C and 6E, respectively. The results of the terpene content analysis of the Hemp samples in Examples 4, 5 and 6 are illustrated in graphical format in FIGS. 6B, 6D and 6F, respectively.

In comparing Examples 1, 2 and 3 (C-0, C-10 and C-20), it is evident that the terpene content drops precipitously from the control sample (Example 1) to Example 2 that was subjected to the disclosed steam extraction process for 10 minutes. The terpene content further drops from Example 2 to Example 3 that was subjected to the disclosed steam extraction process for an additional 10 minutes (20 minutes in total). Thus, the disclosed primary modification process provides clear advantages in terms of removing terpene content from Marijuana. It is also apparent that increased exposure to the disclosed process at least up to 20 minutes increases the effectiveness of the terpene removal.

Moreover, the Total Potential THC content does not decrease from Example 1 (16.8%) to Example 2 (24.0%) and does not significantly decrease from Example 2 (24.0%) to Example 3 (21.1%). While the Total Potential THC content varies somewhat across Examples 1-3, this believed to be a result of natural variability from one flower to another in the sample. The disclosed processes do not increase the potential THC. The starting potential cannabinoids (THCa+THC) should not change, only the ratio should change, as the acid is decarboxylated and converted to the non-acid form. In this regard, the Marijuana samples (C-0, C-10 and C-20) were all selected from the following sample strain:

| Silver State Relief | LIC#: 3869555309634754229 |
|---|---|
| 175 East Greg Street | Dispensed Jan. 7, 2019 |
| Sparks, NV 89431 | |
| Lot # 0654 9950 7556 4096 | Harvested: Jul. 23, 2018 |
| | Package Date Dec. 27, 2018 |
| | Net Wgt: 1.00 (7.08 g) |
| CBD %: 0.09%, THC %: 28.40%, b-Caryophyllene mg/g: 10.9 mg, a-bisabolol mg/g: 4.3 mg, Limonene mg/g: 2.7 mg | |
| WARNING: | |
| This product contains marijuana and it's potency was tested with an allowable variance of +/−15%. This product may have intoxicating effects and may be habit forming. This product may be unlawful outside of the State of Nevada. | |

As seen in the figure above, the reported amount of THC for the sample strain was actually 28%. None of the flowers selected for C-0, C-10 and C-20 assayed at this level, but Example 2 (24.0%) to Example 3 (21.1%) are closer to the dispensary's reported value of 28%. It is also worth noting that the average of the values in Examples 1 and 2 is about the value in Example 3. Therefore, the data clearly show that the disclosed primary modification process selectively extracts the terpenes from Marijuana while retaining substantially all of the THC potential.

In the Hemp samples, the trend is more stable. In comparing Examples 4, 5 and 6 (H-0, H-10 and H-20), it is evident that the terpene content drops precipitously from the control sample (Example 4) to Examples 5 and 6 that were subjected to the disclosed steam extraction process for 10 and 20 minutes, respectively. Thus, the disclosed primary modification process provides clear advantages in terms of removing terpene content from Hemp. Further, the Total Potential CBD content stays the same from Example 4 (9.3%) to Example 5 (9.3%) and does not significantly decrease from Example 5 (9.3%) to Example 6 (6.2%). The important point is that the potential cannabinoids are largely retained but the terpenes show a 10-fold reduction. Therefore, the data clearly show that the disclosed primary modification process selectively extracts the terpenes from Hemp while retaining substantially all of the CBD potential.

It will be appreciated that the above-disclosed features and functions, or alternatives thereof, may be desirably combined into different compositions, systems or methods. Also, various alternatives, modifications, variations or improvements may be subsequently made by those skilled in the art. As such, various changes may be made without departing from the spirit and scope of this disclosure.

What is claimed is:

1. A modified *Cannabis* product comprising:
cannabinoids; and
at least one volatile unsaturated hydrocarbon,
wherein the modified *Cannabis* product is formed by extracting volatile organic compounds from a *Cannabis* raw plant material to form a purified *Cannabis* product, and then adding the at least one volatile unsaturated hydrocarbon to the purified *Cannabis* product to form the modified *Cannabis* product, and
wherein substantially all of a naturally occurring physical structure and cannabinoid content of the *Cannabis* raw plant material is retained in the purified *Cannabis* product after the extraction and in the modified *Cannabis* product so that the modified *Cannabis* product can be combusted and inhaled in a manner similar to a naturally occurring *Cannabis* product under similar conditions.

2. The modified *Cannabis* product according to claim 1, wherein the at least one volatile unsaturated hydrocarbon is a naturally occurring volatile unsaturated hydrocarbon.

3. The modified *Cannabis* product according to claim 1, wherein the at least one volatile unsaturated hydrocarbon is a specific combination of naturally occurring volatile unsaturated hydrocarbons.

4. The modified *Cannabis* product according to claim 1, wherein the at least one volatile unsaturated hydrocarbon is a non-specific combination of naturally occurring volatile unsaturated hydrocarbons.

5. The modified *Cannabis* product according to claim 1, wherein the at least one volatile unsaturated hydrocarbon is a synthetic volatile unsaturated hydrocarbon.

6. The modified *Cannabis* product according to claim 1, wherein the at least one volatile unsaturated hydrocarbon is a specific combination of synthetic volatile unsaturated hydrocarbons.

7. The modified *Cannabis* product according to claim 1, wherein the at least one volatile unsaturated hydrocarbon is a non-specific combination of synthetic volatile unsaturated hydrocarbons.

8. The modified *Cannabis* product according to claim 1, wherein the at least one volatile unsaturated hydrocarbon is a naturally occurring terpene compound.

9. The modified *Cannabis* product according to claim 1, wherein the at least one volatile unsaturated hydrocarbon is a specific combination of naturally occurring terpene compounds.

10. The modified *Cannabis* product according to claim 1, wherein the at least one volatile unsaturated hydrocarbon is a non-specific combination of naturally occurring terpene compounds.

11. The modified *Cannabis* product according to claim 1, wherein the at least one volatile unsaturated hydrocarbon is a synthetic terpene compound.

12. The modified *Cannabis* product according to claim 1, wherein the at least one volatile unsaturated hydrocarbon is a specific combination of synthetic terpene compounds.

13. The modified *Cannabis* product according to claim 1, wherein the at least one volatile unsaturated hydrocarbon is a non-specific combination of synthetic terpene compounds.

14. The modified *Cannabis* product according to claim 1, wherein the at least one volatile unsaturated hydrocarbon is a naturally occurring terpenoid compound.

15. The modified *Cannabis* product according to claim 1, wherein the at least one volatile unsaturated hydrocarbon is a specific combination of naturally occurring terpenoid compounds.

16. The modified *Cannabis* product according to claim 1, wherein the at least one volatile unsaturated hydrocarbon is a non-specific combination of naturally occurring terpenoid compounds.

17. The modified *Cannabis* product according to claim 1, wherein the at least one volatile unsaturated hydrocarbon is a synthetic terpenoid compound.

18. The modified *Cannabis* product according to claim 1, wherein the at least one volatile unsaturated hydrocarbon is a specific combination of synthetic terpenoid compounds.

19. The modified *Cannabis* product according to claim 1, wherein the at least one volatile unsaturated hydrocarbon is a non-specific combination of synthetic terpenoid compounds.

20. The modified *Cannabis* product according to claim 1, wherein the at least one volatile unsaturated hydrocarbon is a naturally occurring essential oil compound.

21. The modified *Cannabis* product according to claim 1, wherein the at least one volatile unsaturated hydrocarbon is a specific combination of naturally occurring essential oil compounds.

22. The modified *Cannabis* product according to claim 1, wherein the at least one volatile unsaturated hydrocarbon is a non-specific combination of naturally occurring essential oil compounds.

23. The modified *Cannabis* product according to claim 1, wherein the at least one volatile unsaturated hydrocarbon is a synthetic essential oil compound.

24. The modified *Cannabis* product according to claim 1, wherein the at least one volatile unsaturated hydrocarbon is a specific combination of synthetic essential oil compounds.

25. The modified *Cannabis* product according to claim 1, wherein the at least one volatile unsaturated hydrocarbon is a non-specific combination of synthetic essential oil compounds.

26. The modified *Cannabis* product according to claim 1, wherein the at least one volatile unsaturated hydrocarbon is a naturally occurring ester compound.

27. The modified *Cannabis* product according to claim 1, wherein the at least one volatile unsaturated hydrocarbon is a specific combination of naturally occurring ester compounds.

28. The modified *Cannabis* product according to claim 1, wherein the at least one volatile unsaturated hydrocarbon is a non-specific combination of naturally occurring ester compounds.

29. The modified *Cannabis* product according to claim 1, wherein the at least one volatile unsaturated hydrocarbon is a synthetic ester compound.

30. The modified *Cannabis* product according to claim 1, wherein the at least one volatile unsaturated hydrocarbon is a specific combination of synthetic ester compounds.

31. The modified *Cannabis* product according to claim 1, wherein the at least one volatile unsaturated hydrocarbon is a non-specific combination of synthetic ester compounds.

32. The modified *Cannabis* product according to claim 1, wherein the at least one volatile unsaturated hydrocarbon is a naturally occurring aldehyde compound.

33. The modified *Cannabis* product according to claim 1, wherein the at least one volatile unsaturated hydrocarbon is a specific combination of naturally occurring aldehyde compounds.

34. The modified *Cannabis* product according to claim 1, wherein the at least one volatile unsaturated hydrocarbon is a non-specific combination of naturally occurring aldehyde compounds.

35. The modified Cannabis product according to claim 1, wherein the at least one volatile unsaturated hydrocarbon is a synthetic aldehyde compound.

36. The modified Cannabis product according to claim 1, wherein the at least one volatile unsaturated hydrocarbon is a specific combination of synthetic aldehyde compounds.

37. The modified Cannabis product according to claim 1, wherein the at least one volatile unsaturated hydrocarbon is a non-specific combination of synthetic aldehyde compounds.

38. The modified Cannabis product according to claim 1, wherein the at least one volatile unsaturated hydrocarbon is a naturally occurring alcohol compound.

39. The modified Cannabis product according to claim 1, wherein the at least one volatile unsaturated hydrocarbon is a specific combination of naturally occurring alcohol compounds.

40. The modified Cannabis product according to claim 1, wherein the at least one volatile unsaturated hydrocarbon is a non-specific combination of naturally occurring alcohol compounds.

41. The modified Cannabis product according to claim 1, wherein the at least one volatile unsaturated hydrocarbon is a synthetic alcohol compound.

42. The modified Cannabis product according to claim 1, wherein the at least one volatile unsaturated hydrocarbon is a specific combination of synthetic alcohol compounds.

43. The modified Cannabis product according to claim 1, wherein the at least one volatile unsaturated hydrocarbon is a non-specific combination of synthetic alcohol compounds.

44. The modified Cannabis product according to claim 1, wherein the Cannabis raw plant material is Marijuana.

45. The modified Cannabis product according to claim 1, wherein the Cannabis raw plant material is Hemp.

46. A method for producing a modified Cannabis product, the method comprising:
   selectively extracting volatile organic compounds from a Cannabis raw plant material to form a purified Cannabis product; and
   adding at least one volatile organic compound to the purified Cannabis product to form the modified Cannabis product,
   wherein the purified Cannabis product is substantially free of terpene content, and
   wherein substantially all of a naturally occurring physical structure and cannabinoid content of the Cannabis raw plant material is retained in the purified Cannabis product after the extraction and in the modified Cannabis product so that the modified Cannabis product can be combusted and inhaled in a manner similar to a naturally occurring Cannabis product under similar conditions.

47. The method for producing a modified Cannabis product according to claim 46, wherein the at least one volatile organic compound is a volatile unsaturated hydrocarbon.

48. The method for producing a modified Cannabis product according to claim 46, wherein the at least one volatile organic compound is at least one compound selected from the group consisting of terpenes, terpenoids, aldehydes, esters, alcohols, and essential oils from a naturally occurring source.

49. The method for producing a modified Cannabis product according to claim 46, wherein a plurality of volatile organic compounds are added to the purified Cannabis product.

50. The method for producing a modified Cannabis product according to claim 46, further comprising determining the plurality of volatile organic compounds to be added to the purified Cannabis product based on historical user data.

51. The method for producing a modified Cannabis product according to claim 50, wherein the historical user data includes a plurality of profiles each representing a specific combination of volatile organic compounds added to the purified Cannabis product.

52. The method for producing a modified Cannabis product according to claim 50, wherein the historical user data includes preferences for at least one of odor and flavor.

53. The method for producing a modified Cannabis product according to claim 46, wherein the modified Cannabis product has reduced odor compared to a reference Cannabis product having at least some terpene content modified under similar conditions.

54. The method for producing a modified Cannabis product according to claim 46, wherein the modified Cannabis product has increased flavor compared to a reference Cannabis product having at least some terpene content modified under similar conditions.

55. A method for producing a modified Cannabis product, the method comprising:
   extracting a first volatile organic compound from a Cannabis raw plant material to form a purified Cannabis product;
   then adding at least one second volatile organic compound to the purified Cannabis product to form the modified Cannabis product,
   wherein the second volatile organic compound is different than the first volatile organic compound, and
   wherein substantially all of a naturally occurring physical structure and cannabinoid content of the Cannabis raw plant material is retained in the purified Cannabis product after the extraction and in the modified Cannabis product so that the modified Cannabis product can be combusted and inhaled in a manner similar to a naturally occurring Cannabis product under similar conditions.

56. The method for producing a modified Cannabis product according to claim 55, wherein the first volatile organic compound is a terpene compound and substantially all of the terpene compound is extracted from the Cannabis raw plant material.

57. The method for producing a modified Cannabis product according to claim 55, wherein adding at least one second volatile organic compound to the purified Cannabis product to form the modified Cannabis product at least one of reduced odor and increased or modified flavor compared to a reference Cannabis product modified under similar conditions without the extraction step.

* * * * *